(12) United States Patent
Bohlmann et al.

(10) Patent No.: US 6,495,607 B2
(45) Date of Patent: Dec. 17, 2002

(54) BENZOCYCLOHEPTENES, PROCESS FOR THEIR PRODUCTION, PHARMACEUTICAL PREPARATIONS THAT CONTAIN THE LATTER AS WELL AS THEIR USE FOR THE PRODUCTION OF PHARMACEUTICAL AGENTS

(75) Inventors: Rolf Bohlmann, Berlin (DE); Jorg Kroll, Berlin (DE); Hermann Kuenzer, Berlin (DE); Christa Hegele-Hartung, Muelheim a. d. Ruhr (DE); Monika Lessl, Berlin (DE); Rosemarie Lichtner, Berlin (DE); Yukishige Nishino, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 09/357,239

(22) Filed: Jul. 19, 1999

(65) Prior Publication Data

US 2002/0068765 A1 Jun. 6, 2002

(30) Foreign Application Priority Data

Jul. 18, 1998 (DE) .......................... 198 33 786

(51) Int. Cl.[7] ...................... A61K 31/095; A61K 31/10; C07C 233/64; C07C 291/00
(52) U.S. Cl. ...................... 514/706; 514/708; 514/759; 514/741; 564/139; 568/27; 568/28; 568/30
(58) Field of Search .................. 514/706, 708, 514/709, 741, 743, 755, 759; 568/27, 28, 30, 34, 35, 36; 564/139

(56) References Cited

FOREIGN PATENT DOCUMENTS

| DE | 19806357 | * | 2/1998 |
|---|---|---|---|
| WO | 96 21656 | | 7/1996 |
| WO | 98/07740 | * | 2/1998 |

OTHER PUBLICATIONS

William Catherino et al . Increased Estrogenicity of a Tamoxifen Analog, Molecular Endocrinology 1995, vol. 9 #8, 1995.*
C.K. Osborne et al., *Cancer Chemotherapy and Pharmacology.*, vol. 34, No. 2, pp. 89–95 (Aug. 1994).
C.S. Murphy et al., *Molecular Pharmacology*, vol. 39, No. 2, pp. 421–828 (Mar. 1991).
R. McCague et al., *Journal of Medicinal Chemistry*, vol. 31, No. 7, pp. 1285–1290 (Jul. 1988).
G.M. Anstead et al., *Journal of Medicinal Chemistry*, vol. 31, No. 7, pp. 1316–1326 (Jul. 1988).
R. McCague et al., *Journal of Medicinal Chemistry*, vol. 29, No. 10, pp. 2053–2059 (Oct. 1988).
International Search Report mailed Nov. 19, 1999.

* cited by examiner

Primary Examiner—Alan L. Rotman
Assistant Examiner—Rita Desai
(74) Attorney, Agent, or Firm—Millen, White, Zelano & Branigan, P.C.

(57) ABSTRACT

Benzocycloheptenes of general formula I

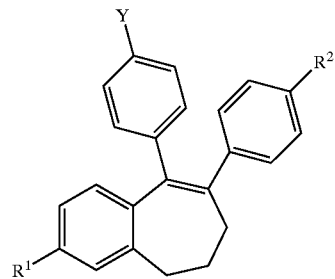

in which $R^1$, $R^2$ and Y have the meanings indicated herein, have antiestrogenic activity on and are suitable for the production of pharmaceutical agents, especially for prophylaxis and therapy of osteoporosis.

28 Claims, No Drawings

BENZOCYCLOHEPTENES, PROCESS FOR THEIR PRODUCTION, PHARMACEUTICAL PREPARATIONS THAT CONTAIN THE LATTER AS WELL AS THEIR USE FOR THE PRODUCTION OF PHARMACEUTICAL AGENTS

This invention relates to benzocycloheptenes of general formula I

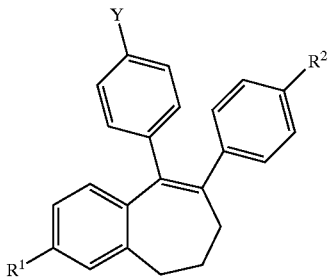

in which
$R^1$ and $R^2$, independently of one another, stand for a hydrogen atom, a hydroxy group, an optionally substituted $C_1$–$C_{10}$ alkoxy group, an optionally substituted $C_1$–$C_{10}$ alkanoyloxy group or an optionally substituted $C_7$–$C_{15}$ aroyloxy group, and Y stands for a side chain —A—B—Z, whereby
A means a direct bond or an oxygen atom,
B means a straight-chain or branched-chain, optionally substituted alkylene, alkenylene or alkinylene group with up to 10 carbon atoms,
Z means a group —D—SO$_x$—E—G, an amino group —NR$^7$R$^8$ or a substituent G, in which
D means a direct bond or a group —NR$^3$(R$^4$—), R$^3$ means a straight-chain or branched-chain alkyl, alkenyl or alkinyl group with up to 10 carbon atoms and R$^4$ means a straight-chain or branched-chain, optionally substituted alkylene, alkenylene or alkinylene group with up to 10 carbon atoms, whereby the nitrogen atom also can be incorporated in a 4- to 7-membered ring system,
the nitrogen atom can also be incorporated into a 4- to 7-membered ring system,
x means 0, 1 or 2,
E means a straight-chain or branched-chain, optionally substituted alkylene, alkenylene or alkinylene group with up to 10 carbon atoms,
G means a partially or completely fluorinated, straight-chain or branched-chain alkyl group with up to 5 carbon atoms, an optionally substituted aryl or heteroaryl radical, a carbamoyl radical —C(O)—NR$^5$R$^6$ with R$^5$ and R$^6$ in the meaning of R$^7$ and R$^8$, a halogen atom or a hydrogen atom,
$R^7$ and $R^8$, independently of one another, mean a hydrogen atom, a straight-chain or branched-chain, optionally partially fluorinated alkyl, alkenyl or alkinyl radical with up to 14 carbon atoms, which can be interrupted by one to three heteroatoms —O— and —S— and groupings —NR$^9$—, in which R$^9$ means a hydrogen atom or a $C_1$–$C_3$ alkyl radical, an aryl or heteroaryl radical that is optionally substituted in one or two places, a $C_3$–$C_{10}$ cycloalkyl radical that is optionally substituted in one or two places, a $C_4$–$C_{15}$ cycloalkylalkyl radical that is optionally substituted in one or two places, a $C_7$–$C_{20}$ aralkyl radical that is optionally substituted in one or two places, a heteroaryl-$C_1$–$C_8$ alkyl radical that is optionally substituted in one or two places or an optionally substituted aminoalkyl radical, a biphenylene radical or a radical of formula —C(O)R$^{10}$, in which R$^{10}$ can have the meanings that are indicated above for R$^7$ or R$^8$, $R^7$ and $R^8$ with the nitrogen atom, to which they are bonded, form a saturated or unsaturated heterocycle with 5 or 6 chain links, which optionally contains one or two additional heteroatoms, selected from nitrogen, oxygen and sulfur, and optionally is substituted, and in —A—B—Z, if A stands for an oxygen atom and Z stands for G, G cannot be a hydrogen atom or a halogen atom, or if A stands for an oxygen atom and Z stands for an amino group —NR$^7$R$^8$, in which R$^7$ and R$^8$ in each case mean a methyl group or together with the nitrogen atom form a pyrrolidine ring, B has at least 3 carbon atoms.

As a $C_1$–$C_{10}$ alkoxy group $R^1$ or $R^2$, for example, a methoxy, ethoxy, propoxy, isopropoxy, butoxy, isobutoxy, tert-butoxy, pentoxy, isopentoxy, neopentoxy, heptyloxy, hexyloxy or decyloxy group is suitable.

The alkanoyl groups that are contained in $R_1$ and $R^2$ of general formula I are to contain 1 to 20 carbon atoms in each case, whereby formyl, acetyl, propionyl and isopropionyl groups are preferred.

Aroyl radicals $R^1$ or $R^2$ are primarily benzoates and benzoates that are substituted in the phenyl radical; they can also be the other aroyl and heteroaroyl radicals that are derived from the aryl radicals that are explained in more detail below.

For B, primarily a straight-chain alkylene group with 1 to 6 carbon atoms is suitable.

As alkyl groups $R^3$, $R^7$ and $R^8$, straight-chain or branched-chain alkyl groups with up to 10 carbon atoms can be considered, such as, for example, methyl, ethyl, propyl, isopropyl, butyl, isobutyl, tert-butyl, pentyl, isopentyl, neopentyl, heptyl, hexyl, decyl.

The latter can have up to 3 unsaturations (double bonds and/or triple bonds).

Alkyl groups $R^3$, $R^7$ and $R^8$ can be partially or completely fluorinated or substituted.

As a partially or completely fluorinated straight-chain or branched $C_1$–$C_{10}$ alkyl group, for example, the trifluoromethyl group, pentafluoroethyl group, 2,2,2-trifluoroethyl group, 4,4,4-trifluorobutyl group, 3,3,4,4,4-pentafluorobutyl group, 4,4,5,5,5-pentafluoropentyl group or nonafluorobutyl group can be mentioned.

The latter can also have up to 3 unsaturations (double bonds and/or triple bonds).

The $C_1$–$C_3$ alkyl radical that stands for $R^9$ is a methyl, ethyl, propyl or isopropyl radical; the methyl radical is preferred.

For aryl radical $R^3$ or $R^4$ and G and the aryl radical within arylalkyl radical $R^3$ or $R^4$, the following radicals that are optionally substituted in one or more places can stand for:
a monocyclic, carbocyclic radical, for example the phenyl radical;
a monocyclic, heterocyclic radical, for example the thienyl, furyl, pyrrolyl, imidazolyl, pyrazolyl, pyridyl, pyrazinyl, pyrimidinyl, pyridazinyl, thiazolyl, oxazolyl, furazanyl, pyrrolinyl, imidazolinyl, pyrazolinyl, thiazolinyl, triazolyl, tetrazolyl radical, specifically all possible isomers relative to the positions of the heteroatoms as well as the interface sites to the sulfur atom in the side chain;

a condensed carbocyclic radical, for example the naphthyl or phenanthrenyl radical;

a condensed radical, which consists of carbocyclic and heterocyclic radicals, for example the benzofuranyl, benzothienyl, benzimidazolyl, benzothiazolyl, naphtho[2,3-b]thienyl, thianthrenyl, isobenzofuranyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, acridinyl, phenazinyl, phenothiazinyl, phenoxazinyl, indolinyl, isoindolinyl, imidazopyridyl, imidazopyrimidinyl or a condensed polyheterocyclic system, for example furo[2,3-b]pyrrole or thieno[2,3-b]furan.

As substituents to radicals B, G, $R^3$, $R^4$, $R^5$, $R^6$, $R^7$, $R^8$ and $R^{10}$ as well as $R^3$ together with $R^4$, the substituents below are suitable, whereby the radicals can be substituted in one or more places, identically or differently, with these substituents:

Halogen atoms: fluorine, chlorine, bromine, iodine;

amino-, mono($C_{1-8}$ alkyl)- or di($C_{1-8}$ alkyl)amino, whereby both alkyl groups are identical or different, especially methylamino or ethylamino, dimethylamino, diethylamino or methylethylamino; di(aralkyl)amino, whereby both aralkyl groups are identical or different;

hydroxyl groups;

free, esterified carboxyl groups or carboxyl groups that are present in the form of a salt: esterified with a carboxycarbonyl group, for example methoxycarbonyl or ethoxycarbonyl; as salt, for example in the form of sodium or potassium salt;

alkyl groups with 1 to 8 carbon atoms, such as, for example, the methyl, ethyl, n- or iso-propyl, n-, iso- or tert-butyl group, optionally substituted with one or more halogen atoms, for example with fluorine, such as the trifluoromethyl or pentafluoroethyl group;

oxo, azido, cyano, nitro or formyl groups;

acyl groups such as acetyl, propionyl, butyryl, benzoyl;

acyloxy groups such as acetoxy, radicals of formula —O—CO—$(CH_2)_n$—COOH with n=1 to 5;

$C_1$–$C_4$ alkoxy groups, such as, for example, methoxy, ethoxy, propoxy, isopropoxy, butoxy;

alkylthio groups, for example methylthio, ethylthio, propylthio, isopropylthio, butylthio, all optionally fluorinated, carbamoyl groups;

alkenyl groups, for example vinyl, propenyl;

alkinyl groups, for example ethinyl, propinyl;

$C_6$–$C_{12}$ aryl groups, such as phenyl, furyl, thienyl, which in turn can be substituted in one to three places.

As a cycloalkyl group for substituents $R^7$ and $R^8$, substituted and unsubstituted radicals with 3 to 10 carbon atoms are suitable; mainly the cyclopropyl and cyclopentyl groups and, as an alkylcyclolalkyl group, the methylcyclopropyl and methylcyclopentyl groups can be mentioned.

The $C_7$–$C_{20}$ aralkyl radicals in $R^7$ and $R^8$ can contain up to 14 C atoms, preferably 6 to 10 C atoms, in the ring, and 1 to 8, preferably 1 to 4 C atoms in the alkyl chain.

As a heteroaryl part, a heteroaryl-$C_1$–$C_8$ alkyl radical in $R^7$ and $R^8$ has one of the already mentioned heteroaryl radicals; the alkyl chain comes with 1 to 8, preferably 1 to 4 C-atoms.

As aralkyl radicals, for example, benzyl, phenylethyl, naphthylmethyl, and napthylethyl are suitable, and as heteroaryl-alkyl radicals, furylmethyl, thienylethyl and pyridylpropyl are suitable.

The rings can be substituted in one or more places.

If $R^7$ and $R^8$ with the nitrogen atom, to which they are bonded, contain a saturated or unsaturated heterocycle with 5 or 6 chain links, which optionally contains one or two additional heteroatoms, selected from nitrogen, oxygen and sulfur, this is especially a pyrrolidine, piperidine, morpholine or piperazine ring.

As substituents for aryl, heteroaryl, aralkyl and heteroarylalkyl radicals, there can be mentioned especially a trifluoromethyl, pentafluoroethyl, trifluoromethylthio, methoxy, ethoxy, nitro, cyano, halogen (fluorine, chlorine, bromine, iodine), hydroxy, amino, mono($C_{1-8}$ alkyl) or di($C_{1-8}$ alkyl)amino, whereby both alkyl groups are identical or different, di(aralkyl)amino, whereby both aralkyl groups are identical or different, or the 1-methoxyacetylamino radical.

The sulfur atom in the side chain can be present as a single sulfur bridge (sulfide), as a sulfone or sulfoxide.

Free hydroxy groups in the compounds of general formula I can be modified functionally, for example by etherification or esterification; free hydroxy groups are preferred, however.

As ether and acyl radicals (protective groups), the radicals that are known to one skilled in the art, such as, e.g., the methoxymethyl, methoxyethyl, ethoxyethyl, tetrahydropyranyl, tetrahydrofuranyl, trimethylsilyl, triethylsilyl, tert-butyldimethylsilyl, tert-butyldiphenylsilyl, tribenzylsilyl, triisopropylsilyl, methyl, tert-butyl, benzyl, para-nitrobenzyl, para-methoxybenzyl, formyl, acetyl, propionyl, isopropionyl, butyryl, pivalyl, benzoyl radicals are suitable. A survey is found in, e.g., "Protective Groups in Organic Synthesis," Theodora W. Green, John Wiley and Sons).

As specific side chains, in which A stands for an oxygen atom, there can be mentioned

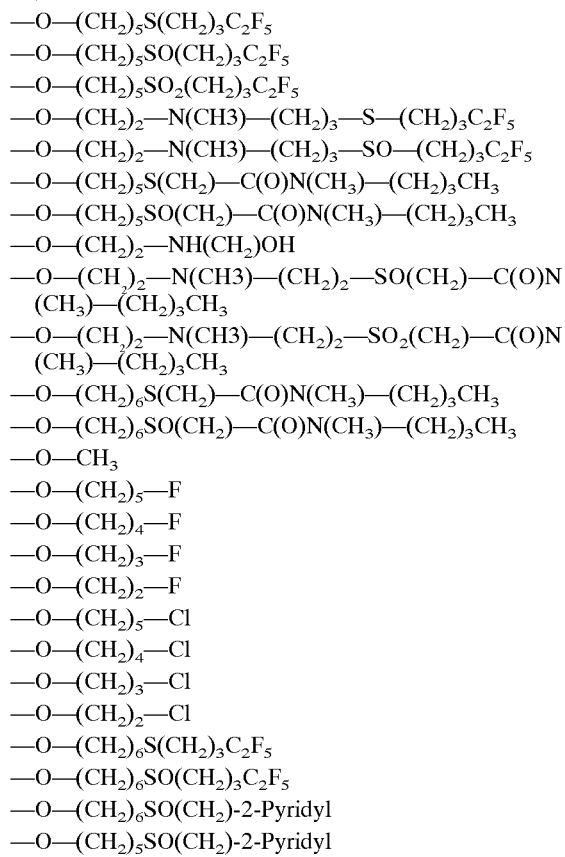

—O—$(CH_2)_5$S$(CH_2)_3$$C_2F_5$

—O—$(CH_2)_5$SO$(CH_2)_3$$C_2F_5$

—O—$(CH_2)_5$$SO_2$$(CH_2)_3$$C_2F_5$

—O—$(CH_2)_2$—N(CH3)—$(CH_2)_3$—S—$(CH_2)_3$$C_2F_5$

—O—$(CH_2)_2$—N(CH3)—$(CH_2)_3$—SO—$(CH_2)_3$$C_2F_5$

—O—$(CH_2)_5$S$(CH_2)$—C(O)N$(CH_3)$—$(CH_2)_3$$CH_3$

—O—$(CH_2)_5$SO$(CH_2)$—C(O)N$(CH_3)$—$(CH_2)_3$$CH_3$

—O—$(CH_2)_2$—NH$(CH_2)$OH

—O—$(CH_2)_2$—N(CH3)—$(CH_2)_2$—SO$(CH_2)$—C(O)N$(CH_3)$—$(CH_2)_3$$CH_3$

—O—$(CH_2)_2$—N(CH3)—$(CH_2)_2$—$SO_2$$(CH_2)$—C(O)N$(CH_3)$—$(CH_2)_3$$CH_3$

—O—$(CH_2)_6$S$(CH_2)$—C(O)N$(CH_3)$—$(CH_2)_3$$CH_3$

—O—$(CH_2)_6$SO$(CH_2)$—C(O)N$(CH_3)$—$(CH_2)_3$$CH_3$

—O—$CH_3$

—O—$(CH_2)_5$—F

—O—$(CH_2)_4$—F

—O—$(CH_2)_3$—F

—O—$(CH_2)_2$—F

—O—$(CH_2)_5$—Cl

—O—$(CH_2)_4$—Cl

—O—$(CH_2)_3$—Cl

—O—$(CH_2)_2$—Cl

—O—$(CH_2)_6$S$(CH_2)_3$$C_2F_5$

—O—$(CH_2)_6$SO$(CH_2)_3$$C_2F_5$

—O—$(CH_2)_6$SO$(CH_2)$-2-Pyridyl

—O—$(CH_2)_5$SO$(CH_2)$-2-Pyridyl

—O—(CH$_2$)$_5$S(CH$_2$)$_2$C$_3$F$_7$
—O—(CH$_2$)$_2$-1-Pyrrolidinyl
—O—(CH$_2$)$_4$S(CH$_2$)$_3$C$_2$F$_5$
—O—(CH$_2$)$_4$SO(CH$_2$)$_3$C$_2$F$_5$
—O—(CH$_2$)$_4$SO$_2$(CH$_2$)$_3$C$_2$F$_5$
—O—(CH$_2$)$_4$S(CH$_2$)-2-Pyridyl
—O—(CH$_2$)$_4$SO(CH$_2$)-2-Pyridyl
—O—(CH$_2$)$_5$S(CH$_2$)-2-Pyridyl
—O—(CH$_2$)$_5$SO(CH$_2$)-2-Pyridyl
—O—(CH$_2$)$_6$S(CH$_2$)-2-Pyridyl
—O—(CH$_2$)$_6$SO(CH$_2$)-2-Pyridyl
—O—(CH$_2$)$_5$S(CH$_2$)-2-Furyl
—O—(CH$_2$)$_5$SO(CH$_2$)-2-Furyl
—O—(CH$_2$)$_5$SO$_2$(CH$_2$)-2-Furyl
—O—(CH$_2$)$_5$S(CH$_2$)-2-Thienyl
—O—(CH$_2$)$_5$SO(CH$_2$)-2-Thienyl
—O—(CH$_2$)$_5$S(CH$_2$)$_4$—F
—O—(CH$_2$)$_5$SO(CH$_2$)$_4$—F
—O—(CH$_2$)$_5$S(CH$_2$)$_3$—CF$_3$
—O—(CH$_2$)$_5$SO(CH$_2$)$_3$—CF$_3$
—O—(CH$_2$)$_5$—N(CH$_3$)—(CH$_2$)$_3$—C$_2$F$_5$
—O—(CH$_2$)$_5$S(CH$_2$)-Phenyl
—O—(CH$_2$)$_5$SO(CH$_2$)-2-Phenyl
—O—(CH$_2$)$_5$S(CH$_2$)-p-Tolyl
—O—(CH$_2$)$_5$SO(CH$_2$)-p-Tolyl
—O—(CH$_2$)$_5$S(CH$_2$)-p-CF$_3$-Phenyl
—O—(CH$_2$)$_5$SO(CH$_2$)-p-CF$_3$-Phenyl
—O—(CH$_2$)$_5$S-Phenyl
—O—(CH$_2$)$_5$SO-Phenyl
—O—(CH$_2$)$_5$S—(p-Tolyl)
—O—(CH$_2$)$_5$SO—(p-Tolyl)
—O—(CH$_2$)$_5$S—(p-CF$_3$-Phenyl)
—O—(CH$_2$)$_5$SO—(p-CF$_3$-Phenyl)
—O—(CH$_2$)$_2$—N(CH$_3$)$_2$ As side chains, in which A stands for a direct bond, for example, the following are suitable (DE 1 98 06 357.1)

—(CH$_2$)$_5$N(CH$_3$)(CH$_2$)$_3$C$_2$F$_5$
—(CH$_2$)$_5$N(CH$_3$)(CH$_2$)$_6$C$_2$F$_5$
—(CH$_2$)$_5$N(CH$_3$)(CH$_2$)$_7$C$_2$F$_5$
—(CH$_2$)$_5$N(CH$_3$)(CH$_2$)$_8$C$_2$F$_5$
—(CH$_2$)$_6$N(CH$_3$)(CH$_2$)$_6$C$_2$F$_5$
—(CH$_2$)$_6$N(CH$_3$)(CH$_2$)$_7$C$_2$F$_5$
—(CH$_2$)$_6$N(CH$_3$)(CH$_2$)$_8$C$_2$F$_5$
—(CH$_2$)$_5$N(CH$_3$)(CH$_2$)$_2$C$_4$F$_9$
—(CH$_2$)$_5$N(CH$_3$)(CH$_2$)$_3$C$_6$F$_{13}$
—(CH$_2$)$_5$N(CH$_3$)(CH$_2$)$_3$C$_8$F$_{17}$
—(CH$_2$)$_5$N(CH$_3$)(CH$_2$)$_6$C$_4$F$_9$
—(CH$_2$)$_5$N(CH$_3$)(CH$_2$)$_6$C$_6$F$_{13}$
—(CH$_2$)$_5$N(CH$_3$)(CH$_2$)$_6$C$_8$F$_{17}$
—(CH$_2$)$_5$N(CH$_3$)H
—(CH$_2$)$_5$N(CH$_3$)(CH$_2$)$_9$H
—(CH$_2$)$_5$-1-Pyrrolidinyl
—(CH$_2$)$_9$S(CH$_2$)$_3$C$_2$F$_5$
—(CH$_2$)$_9$SO(CH$_2$)$_3$C$_2$F$_5$
—(CH$_2$)$_9$SO$_2$(CH$_2$)$_3$C$_2$F$_5$.

In addition, the side chains of general partial formula

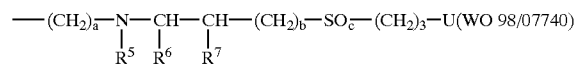

are suitable whereby a is 4, 5 or 6,
b is 0, 1 or 2,
c is 0, 1 or 2,
$R^5$ is a hydrogen atom or a $C_{1-5}$ alkyl group,
$R^6$ and $R^7$ are each a hydrogen atom, or
$R^5$ and $R^6$ together are an alkylene group —(CH$_2$)$_d$— with d=2, 3, 4 or 5, and $R^7$ is a hydrogen atom or
$R^5$ and $R^7$ together are an alkylene group —(CH$_2$)$_e$— with e=2, 3 or 4 and $R^6$ is a hydrogen atom, and
U is an unsubstituted ethyl radical or an ethyl radical that is fluorinated in one to five places, or
the terminal substituent —(CH$_2$)$_3$—U in the side chain is replaced by an optionally substituted aryl or heteroaryl radical, which is bonded directly or via a mono-, di- or trimethylene group to the sulfur atom, and of the latter in turn especially the side chains
—(CH$_2$)$_5$N(CH$_3$)(CH$_2$)$_3$S(CH$_2$)$_3$C$_2$F$_5$ and
—(CH$_2$)$_5$N(R$^5$)(CHR$^6$)CH$_2$S(CH$_2$)$_3$C$_2$F$_5$ with R$^5$+R$^6$=—(CH$_2$)$_3$—.

For the purposes of this invention, the preferred compounds are (4,4,5,5,5-Pentafluoropentyl)-{5-[4-(6-phenyl-8,9-dihydro-7H-benzocyclohepten-5-yl)-phenoxy]-pentyl}-sulfide (4,4,5,5,5-pentafluoropentyl)-{5-[4-(6-phenyl-8,9-dihydro-7H-benzocyclohepten-5-yl)-phenoxy]-pentyl}-sulfoxide methyl-[3-(4,4,5,5,5-pentafluoropentylthio)-propyl]-{2-[4-(6-phenyl-8,9-dihydro-7H-benzocyclohepten-5-yl)-phenoxy]-ethyl}-amine methyl-[3-(4,4,5,5,5-pentafluoropentylsulfinyl)-propyl]-{2-[4-(6-phenyl-8,9-dihydro-7H-benzocyclohepten-5-yl)-phenoxy]-ethyl}-amine S-{5-[4-(6-phenyl-8,9-dihydro-7H-benzocyclohepten-5-yl)-phenoxy]-pentyl}-thioacetate N-butyl-N-methyl-2-{5-[4-(6-phenyl-8,9-dihydro-7H-benzocyclohepten-5-yl)-phenoxy]-pentylthio}-acetamide N-butyl-N-methyl-2-{5-[4-(6-phenyl-8,9-dihydro-7H-benzocyclohepten-5-yl)-phenoxy)-pentanesulfinyl}-acetamide 5-{4-[5-(4,4,5,5,5-pentafluoro-pentylthio)-pentyloxy]-phenyl}-6-phenyl-8,9-dihydro-7H-benzocyclohepten-2-ol 5-{4-[5-(4,4,5,5,5-pentafluoro-pentanesulfinyl)-pentyloxy]-phenyl}-6-phenyl-8,9-dihydro-7H-benzocyclohepten-2-ol 5-[4-(2-{methyl-[3-(4,4,5,5,5-pentafluoro-pentanesulfinyl)-propyl]-amino}-ethoxy)-phenyl]-6-phenyl-8,9-dihydro-7H-benzocyclohepten-2-ol 5-[4-(2-{methyl-[3-(4,4,5,5,5-pentafluoro-pentylthio)-propyl]-amino}-ethoxy)-phenyl]-6-phenyl-8,9-dihydro-7H-benzocyclohepten-2-ol N-butyl-N-methyl-2-{5-[4-(2-hydroxy-6-phenyl-8,9-dihydro-7H-benzocyclohepten-5-yl)-phenoxy]-pentylthio}-acetamide 5-{4-[5-(4,4,5,5,5-pentafluoro-pentanesulfonyl)-pentyloxy]-phenyl}-6-phenyl-8,9-dihydro-7H-benzocyclohepten-2-ol N-butyl-N-methyl-2-{5-[4-(2-hydroxy-6-phenyl-8,9-dihydro-7H-benzocyclohepten-5-yl)-phenoxy]-pentanesulfinyl}-acetamide N-butyl-2-[2-({2-[4-(2-hydroxy-6-phenyl-8,9-dihydro-7H-benzocyclohepten-5-yl)-phenoxy]-ethyl}-methyl-amino)-ethanesulfinyl]-N-methyl-acetamide N-butyl-2-[2-({2-[4-(2-hydroxy-6-phenyl-8,9-dihydro-7H-benzocyclohepten-5-yl)-phenoxy]-ethyl}-methyl-amino)-ethanesulfonyl]-N-methyl-acetamide 6-(4-hydroxy-phenyl)-5-{4-[5-(4,4,5,5,5-pentafluoro-pentanesulfonyl)-pentyloxy]-phenyl}-8,9-dihydro-7H-benzocyclohepten-2-ol N-butyl-2-{6-[4-(2-hydroxy-6-phenyl-8,9-dihydro-7H-benzocyclohepten-5-yl)-phenoxy]-hexanesulfinyl}-N-methyl-acetamide N-butyl-2-{6-[4-(2-hydroxy-6-phenyl-8,9-dihydro-7H-benzocyclohepten-5-yl)-phenoxy]-hexylthio}-N-methyl-acetamide 6-(4-hydroxy-phenyl)-5-{4-[5-(4,4,5,5,5-pentafluoropentylthio)-pentyloxy]-phenyl}-8,9-dihydro-7H-benzocyclohepten-2-ol 6-(4-hydroxy-phenyl)-5-{4-[5-(4,4,5,5,5-pentafluoropentane-sulfinyl)-pentyloxy]-phenyl}-8,9-dihydro-7H-benzocyclohepten-2-ol 5-{4-[4-(4,4,5,5,5-pentafluoro-pentylthio)-butyloxy]-phenyl}-6-phenyl-8,9-dihydro-7H-benzocyclohepten-2-ol 6-phenyl-5-{4-[4-(pyridin-2-ylmethylthio)-butyloxy]-phenyl}-8,9-dihydro-7H-benzocyclohepten-2-ol 6-phenyl-5-{4-[5-(pyridin-2-ylmethylthio)-pentyloxy]-phenyl}-8,9-dihydro-7H-benzocyclohepten-2-ol 6-phenyl-5-{4-[6-(pyridin-2-ylmethylthio)-hexyloxy]-phenyl}-8,9-dihydro-7H-benzocyclohepten-2-ol 5-{4-[4-(4,4,5,5,5-pentafluoro-pentanesulfinyl)-butyloxy]-phenyl}-6-phenyl-8,9-dihydro-7H-benzocyclohepten-2-ol 6-phenyl-5-{4-[4-(pyridin-2-ylmethanesulfinyl)-butyloxy]-phenyl}-8,9-dihydro-7H-benzocyclohepten-2-ol 5-{4-[6-(4,4,5,5,5-pentafluoro-pentylthio)-hexyloxy]-phenyl}-6-phenyl-8,9-dihydro-7H-benzocyclohepten-2-ol 5-{4-[6-(4,4,5,5,5-pentafluoro-pentanesulfinyl)-hexyloxy]-phenyl}-6-phenyl-8,9-dihydro-7H-benzocyclohepten-2-ol 6-phenyl-5-{4-[6-(pyridin-2-ylmethanesulfinyl)-hexyloxy]-phenyl}-8,9-dihydro-7H-benzocyclohepten-2-ol 6-phenyl-5-{4-[5-(pyridin-2-ylmethanesulfinyl)-pentyloxy]-phenyl}-8,9-dihydro-7H-benzocyclohepten-2-ol 5-{4-[5-(furan-2-ylmethylthio)-pentyloxy]-phenyl}-6-phenyl-8,9-dihydro-7H-benzocyclohepten-2-ol 6-phenyl-5-{4-[5-(thien-2-ylmethylthio)-pentyloxy]-phenyl}-8,9-dihydro-7H-benzocyclohepten-2-ol 5-{4-[5-(furan-2-ylmethanesulfinyl)-pentyloxy]-phenyl}-6-phenyl-8,9-dihydro-7H-benzocyclohepten-2-ol 5-{4-[5-(furan-2-ylmethanesulfonyl)-pentyloxy]-phenyl}-6-phenyl-8,9-dihydro-7H-benzocyclohepten-2-ol 6-phenyl-5-{4-[5-(thien-2-ylmethanesulfonyl)-pentyloxy]-phenyl}-8,9-dihydro-7H-benzocyclohepten-2-ol 6-phenyl-5-{4-[5-(thien-2-ylmethanesulfinyl)-pentyloxy]-phenyl}-8,9-dihydro-7H-benzocyclohepten-2-ol 5-{4-[5-(3,3,4,4,5,5,5-heptafluoro-pentylthio)-pentyloxy]-phenyl}-6-phenyl-8,9-dihydro-7H-benzocyclohepten-2-ol 5-{4-[2-(2-hydroxy-ethylamino)-ethoxy]-phenyl}-6-phenyl-8,9-dihydro-7H-benzocyclohepten-2-ol 5-{4-[5-(4-fluoro-butylthio)-pentyloxy]-phenyl}-6-phenyl-8,9-dihydro-7H-benzocyclohepten-2-ol 5-{4-[5-(4-fluoro-butanesulfinyl)-pentyloxy]-phenyl]-6-phenyl-8,9-dihydro-7H-benzocyclohepten-2-ol 6-phenyl-5-{4-[5-(4,4,4-trifluoro-butylthio)-pentyloxy]-phenyl}-8,9-dihydro-7H-benzocyclohepten-2-ol 6-phenyl-5-{4-[5-(4,4,4-trifluoro-butanesulfinyl)-pentyloxy]-phenyl}-8,9-dihydro-7H-benzocyclohepten-2-ol 5-(4-{5-[methyl-(4,4,5,5,5-pentafluoropentyl)-amino]-pentyloxy}-phenyl)-6-phenyl-8,9-dihydro-7H-benzocyclohepten-2-ol 5-[4-(5-benzylthio-pentyloxy)-phenyl]-6-phenyl-8,9-dihydro-7H-benzocyclohepten-2-ol 5-[4-(5-benzylsulfinyl-pentyloxy)-phenyl]-6-phenyl-8,9-dihydro-7H-benzocyclohepten-2-ol 5-{4-[5-(4-methyl-benzylthio)-pentyloxy]-phenyl}-6-phenyl-8,9-dihydro-7H-benzocyclohepten-2-ol 5-{4-[5-(4-methyl-benzylsulfinyl)-pentyloxy]-phenyl}-6-phenyl-8,9-dihydro-7H-benzocyclohepten-2-ol 6-phenyl-5-{4-[5-(4-trifluoromethyl-benzylthio)-pentyloxy]-phenyl}-8,9-dihydro-7H-benzocyclohepten-2-ol 6-phenyl-5-{4-[5-(4-trifluoromethyl-benzylsulfinyl)-pentyloxy]-phenyl}-8,9-dihydro-7H-benzocyclohepten-2-ol 6-phenyl-5-[4-(5-phenylthio-pentyloxy)-phenyl]-8,9-dihydro-7H-benzocyclohepten-2-ol 6-phenyl-5-[4-(5-phenylsulfinyl-pentyloxy)-phenyl]-8,9-dihydro-7H-benzocyclohepten-2-ol 6-phenyl-5-[4-(5-phenylsulfonyl-pentyloxy)-phenyl]-8,9-dihydro-7H-benzocyclohepten-2-ol 5-{4-[5-(4-tert-butyl-phenylthio)-pentyloxy]-phenyl}-6-phenyl-8,9-dihydro-7H-benzocyclohepten-2-ol 5-{4-[5-(4-tert-butyl-phenylsulfinyl)-pentyloxy]-phenyl}-6-phenyl-8,9-dihydro-7H-benzocyclohepten-2-ol 5-{4-[5-(4-tert-butyl-phenylsulfonyl)-pentyloxy]-phenyl}-6-phenyl-8,9-dihydro-7H-benzocyclohepten-2-ol 6-phenyl-5-{4-[5-(4-trifluoromethyl-phenylthio)-pentyloxy]-phenyl}-8,9-dihydro-7H-benzocyclohepten-2-ol 6-phenyl-5-{4-[5-(4-trifluoromethyl-phenylsulfinyl)-pentyloxy]-phenyl}-8,9-dihydroxy-7H-benzocyclohepten-2-ol 6-phenyl-5-{4-[5-(4-trifluoromethyl-phenylsulfonyl)-pentyloxy]-phenyl}-8,9-dihydro-7H-benzocyclohepten-2-ol.

In addition to these compounds of general formula I, if a nitrogen atom is contained in side chain Y, this invention also relates to their physiologically compatible addition salts with organic and inorganic acids, these compounds of general formula I including the pharmaceutical preparations that contain addition salts as well as their use for the production of pharmaceutical agents.

Inorganic and organic acids, as they are known to one skilled in the art for the formation of physiologically compatible salts, are suitable for the formation of acid addition salts. As addition salts with acids, especially hydrochlorides, hydrobromides, acetates, citrates, oxalates, tartrates and the methanesulfonates can be mentioned.

The compounds of general formula I represent compounds with strong antiestrogenic activity.

The compounds according to the invention are selective estrogens, whose action occurs in a tissue-selective manner. The estrogenic action occurs in particular on bones. No estrogenic action or only a slight estrogenic action occurs in the uterus and in the liver, however.

The compounds can also have antiestrogenic activity, which can be detected, for example, in an anti-uterus growth test or in tumor models. Compounds with such a profile have recently been designated as Selective Estrogen Receptor Modulators (SERMs) (Structure-Activity Relationships of Selective Estrogen Receptor Modulators: Modifications to the 2-Arylbenzothiophene Core of Raloxifene, T. A. Grese et al., J. Med. Chem. 1997, 40, 146–167).

The most prominent representative of this compound class is raloxifene, which is now allowed as a medication for the prevention and the treatment of postmenopausal osteoporosis.

Compounds with antiestrogenic properties, i.e., substances with inhibiting actions relative to estrogens, have already been described extensively. In this case, these are compounds both with a steroidal and with a non-steroidal skeleton.

The tamoxifen that became known for the first time from BE 637,389, (Z)-2-[4-(1,2-diphenyl-1-butenyl)-phenoxy]-N,N-dimethylethylamine, has been used for breast cancer therapy longer than antiestrogen.

Raloxifene, 6-hydroxy-2-(4-hydroxyphenyl)-3-[4-(2piperidinoethoxy)benzoyl]benzo[b]-thiophene, and its hydrochloride can be used for treatment and prophylaxis of osteoporosis (EP 0 584 952 B1).

The steroid derivative 7α-[9-(4,4,5,5,5-pentafluoropentylsulfinyl)-n-nonyl]-estra-1,3,5(10)-triene-3,17β-diol (EP A 0 138 504, page 58, penultimate compound) that became known from EP A 0 138 504 B1 is currently under clinical development for hormone-dependent tumors (breast cancer).

Pharmaceutical compositions, which contain sex steroid inhibitors and which have a steroidal skeleton that has a 7α-side chain in the case of the simultaneous presence of at least one additional substituent in 14-, 15- or 16-position, are the subject of EP-A 0 376 576. This patent application also relates to non-steroidal, antiestrogenic compounds, i.a., the compound EM 800. This compound was described originally as a pure antiestrogen; it has now been found, however, that this compound also has a clear partial estrogenic action.

The estrogen agonists and antagonists that became known from WO 96/21656 are, i.a., benzocyclopentane, hexane and heptane derivatives, which in the aromatic portion carry a hydroxy group, a nitrogen aromatic compound on carbon atom 5 or a phenyl radical that is provided with a side chain in 4-position and a phenyl radical that optionally has a side chain on carbon atom 6, i.a. Compounds with an unsaturation in the slightly condensed structural part are not disclosed there. Actually, merely benzocyclohexane derivatives are described.

Some compounds with a benzocycloheptene basic structure are found in various publications (Mol. Pharmacol. 1991, 39: 421–428; J. Med. Chem., 1986, 29, 2053–2059; J. Med. Chem., 1988, 31, 1316–1326). These compounds have in 4-position the phenyl radical that is bonded to carbon atom 5, a methoxy group, a 2-(dimethylamino)ethoxy group or a 2-(1-pyrrolidinyl)ethoxy group. It is not said of these compounds that they are selective estrogens.

Pharmacological Study of the Compounds According to the Invention

The influence of the compounds according to the invention on the uterus was studied in the uterus growth test (estrogenic action) and in the anti-uterus growth test (antiestrogenic action), both performed on infant rats.

Estrogenic/Antiestrogenic Action in Vivo Uterus Growth Test on Infant Rats (n=5 Animals/Group)

In infant animals, both uterus and vagina show a weight increase that is dependent on the estrogenic activity in their treatment with an estrogenically active substance. In the uterus, under estrogenic action, this results, moreover, in a proliferation and level increase of the luminal epithelium. Immature, normal rats (body weight 40–50 g) receive the substance s.c. over 3 days (d1–d3). On day 4 (d4), the animals are sacrificed with $CO_2$. The uteri are prepared outside and weighed. A piece of the uterus, preferably a uterine horn, is set in formaldehyde for histological evaluation and embedded in paraffin. The stimulation of the organ weights (relative to mg/100 g of body weight) as well as the epithelial level are indicated in percentage stimulation in comparison to the reference compound 17β-estradiol. (Substitution dose $E_2$ 0.3 μg/animal).

The compounds according to the invention have no effect or an only slightly stimulating effect on the uterus.

Antiuterus Growth Test on Infant Rats (n=5 Animals/Group)

The uterus of infant estrogen-substituted rats can be used as a test model to detect a direct action of substances with antiestrogenic properties. The parameter of the estrogen action is the uterus growth that is induced by estradiol in infant rats, which is inhibited by the simultaneous administration of a substance with antiestrogenic action.

The test substances are treated s.c. on 3 successive days (d1–d3) in combination with a substitution dose of 0.3 μg/animal/day of 17β-estradiol. As a positive control, 17β-estradiol is used alone; as a negative control, the vehicle group is used. On day 4 (d4), the animals are sacrificed, uteri and vaginae are prepared outside and weighed. The organ weights are calculated in mg/100 g of body weight, then the mean value and the standard deviation for each dosage is calculated. The inhibition of the uterus or vaginal growth that is induced by 17β-estradiol is indicated as inhibition in %.

The compounds according to the invention for the most part show a clearly pronounced inhibition of the uterus growth that is induced by 17β-estradiol.

Thus with respect to their action on the uterus, the compounds according to the invention are superior to the compounds of the prior art for the purposes of this invention to the extent that they have less or even no estrogenic action on this organ.

Bone Studies
Method 3-month-old female rats are ovariectomized and treated once daily with the test compound immediately after the operation for 28 days. The administration is carried out subcutaneously in peanut oil/ethanol. The animals are sacrificed on the day after the last administration, and tibia as well as uteri are removed. The uteri are weighed, set and worked up for histological studies. The determination of bone density is carried out ex vivo on prepared long bones using pQCT (quantitative computer tomography). The measurements are carried out at a distance of 4–6 mm from the ball of the joint of the proximal tibia.

The density of the trabecular bone in the measured area is reduced by the ovariectomy from about 400 mg of $Ca^{2+}/cm^3$ to about 300 mg of $Ca^{2+}/cm^3$. The degradation of bone density is prevented or inhibited by the treatment with a compound of general formula I according to this invention (dosages of 0.1–100 μg/animal/day). The bone density was measured at the proximal tibia.

With respect to their bone-protective action, the compounds according to the invention have an action that is comparable to the compounds of the prior art in the case of simultaneously weakened or absent uterotrophic estrogenic action.

Thus for the purpose of a selective action on the bone with respect to a weakened action on the uterus, the compounds according to the invention are more greatly dissociated than the compounds of the prior art.

The invention also relates to pharmaceutical preparations, which contain at least one compound of general formula I (or physiologically compatible addition salts with organic and inorganic acids thereof), and the use of these compounds for the production of pharmaceutical agents, especially for the indications below.

The compounds can be used both after oral and parenteral administration for the following indications:

Alleviation of the symptoms of male menopause and female menopause, i.e., for male and female hormone replacement therapy (HRT), specifically both for prevention and for treatment; for treatment of symptoms accompanying a dysmenorrhea; treatment of dysfunctional uterine bleeding; treatment of acne; prevention and treatment of cardiovascular diseases; treatment of hypercholesteremia and hyperlipemia; prevention and treatment of arteriosclerosis; for inhibition of the proliferation of arterial smooth muscle cells; for treatment of the respiratory distress syndrome in newborn children; treatment of primary pulmonary high blood pressure; for prevention and treatment of osteoporosis (Black, L. J.; Sato, M.; Rowley, E. R.; Magee, D. E.; Bekele, A.; Williams, D. C.; Cullinan, G. J.; Bendele, R.; Kauffman, R. F.; Bensch, W. R.; Frolik, C. A.; Termine, J. D. and Bryant, H. U.: Raloxifene [LY 139481 HCl] Prevents Bone Loss and Reduces Serum Cholesterol without Causing Uterine Hypertrophy in Ovariectomized Rats; J. Clin. Invest. 93: 63–69, 1994); for prevention of bone loss in postmenopausal women, in women who have had hysterectomies or in women who were treated with LHRH agonists or antagonists; inhibition of spermatic maturation; treatment of rheumatoid arthritis; for prevention of Alzheimer's disease; treatment of endometriosis; treatment of myomas; treatment of myomas and endometriosis in combination with LHRH analogues; treatment of hormone-dependent tumors, e.g., breast cancer, treatment of prostatic diseases.

In addition, the compounds according to the invention are suitable based on their pharmacological profile both for male and for female contraception.

The compounds can also be used in combination with the natural vitamin D3 or with calcitriol analogues for bone degradation or as supporting therapies to therapies that cause bone mass loss (for example therapy with glucocorticoids, chemotherapy).

Finally, the compounds of general formula I can be used in connection with progesterone receptor antagonists or in connection with pure estrogens, specifically especially for use in hormone replacement therapy and for treatment of gynecological disorders and for female birth control.

A therapeutic product that contains an estrogen and a pure antiestrogen for simultaneous, sequential or separate use of the selective estrogen therapy of perimenopausal or postmenopausal conditions is already described in EP-A 0 346 014.

The amount of a compound of general formula I that is to be administered fluctuates within a wide range and can cover any effective amount. Based on the condition to be treated and the type of administration, the amount of administered compound can be 0.01–10 mg/kg of body weight, preferably 0.1–5 mg/kg of body weight, per day.

In humans, this corresponds to a dose of 0.8 to 800 mg, preferably 8 to 400 mg, daily.

A dosage unit contains, according to the invention, 0.4 to 400 mg of one or more compounds of general formula I.

The compounds according to the invention and the acid addition salts are suitable for the production of pharmaceutical compositions and preparations. The pharmaceutical compositions or pharmaceutical agents contain as active ingredient one or more of the compounds according to the invention or their acid addition salts, optionally mixed with other pharmacologically or pharmaceutically active substances. The production of the pharmaceutical agents is carried out in a known way, whereby the known and commonly used pharmaceutical adjuvants and other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullmans Encyclopedia of Technical Chemistry], Volume 4 (1953), pages 1 to 39; Journal of Pharmaceutical Sciences, Volume 52 (1963), pages 918 ff. issued by Czetsch-Lindenwald, Hilfsstoffe für Pharmazie und angrenzende Gebiete [Adjuvants for Pharmaceutics and Related Fields]; Pharm. Ind., Issue 2, 1961, pages 72 and ff.: Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor K G, Aulendorf in Württemberg 1971.

The compounds can be administered orally or parenterally, for example intraperitoneally, intramuscularly, subcutaneously or percutaneously. The compounds can also be implanted in the tissue.

For oral administration, capsules, pills, tablets, coated tablets, etc. are suitable. In addition to the active ingredient, the dosage units can contain a pharmaceutically compatible vehicle, such as, for example, starch, sugar, sorbitol, gelatin, lubricant, silicic acid, talc, etc.

For parenteral administration, the active ingredients can be dissolved or suspended in a physiologically compatible diluent. As diluents, oils are very frequently used with or without the addition of a solubilizer, a surfactant, a suspending agent or an emulsifier. Examples of oils that are used are olive oil, peanut oil, cottonseed oil, soybean oil, castor oil and sesame oil.

The compounds can also be used in the form of a depot injection or an implant preparation, which can be formulated in such a way that a delayed release of active ingredient is made possible.

As inert materials, implants can contain, for example, biodegradable polymers or synthetic silicones such as, for example, silicone rubber.

In addition, the active ingredients can be added for percutaneous administration, for example, to a patch.

For the production of intravaginal systems (e.g., vaginal rings) or intrauterine systems (e.g., pessaries, coils, IUDs, Mirena®) that are loaded with active compounds of general formula I for local administration, various polymers are suitable, such as, for example, silicon polymers, ethylene vinyl acetate, polyethylene or polypropylene.

To achieve better bioavailability of the active ingredient, the compounds can also be formulated as cyclodextrin clathrates. For this purpose, the compounds are reacted with α-, β- or γ-cyclodextrin or derivatives of the latter (PCT/EP95/02656).

According to the invention, the compounds of general formula I can also be encapsulated with liposomes.

The compounds of general formula I according to the invention are produced as described in the examples. By an analogous procedure using reagents that are homologous to the reagents that are described in the examples, all compounds of general formula I can be obtained.

Etherification and/or esterification of free hydroxy groups is carried out according to the methods that are common to one skilled in the art.

The compounds of general formula I, in which A stands for a direct bond, can be obtained, for example, analogously to the processes that are described in WO 98/07740 and DE 1 98 06 357.1. To introduce side chain SK, first the 4-hydroxy group of the phenyl radical in 5-position of the starting product is converted into a trifluoromethylsulfonyloxy group and then palladium-catalyzed, and an alkylation on the phenyl radical is carried out to introduce terminally functionalized radical B (J. Org. Chem., 58; 8; 1993, pp. 2201–2208; Tetrahedron Lett. 28: 21; 1987, pp. 2387–2388). The further processing for the creation of complete side chain SK is then carried out as described in WO 98/07740 or DE 1 98 06 357.1.

EXAMPLES

Example 1

(4,4,5,5,5-Pentafluoropentyl)-{5-[4-(6-phenyl-8,9-dihydro-7H-benzocyclohepten-5-yl)-phenoxy]-pentyl}-sulfide a) 9-[4-(5-Chloropentyloxy)-phenyl]-8-phenyl-6,7-dihydro-5H-benzocycloheptene A suspension of 3.0 g of 4-(6-phenyl-8,9-dihydro-7H-benzocyclohepten-5-yl)-phenol [Raymond McCague, Reiko Kuroda, Guy Leclerq, Susanna Stoessel, J. Med. Chem. (29) 10 1986 pp. 2053–2059] in 51 ml of acetonitrile is stirred with 1.68 g of potassium carbonate and 1.49 ml of 1-bromo-5-chloropentane for 9 hours at 100° C. Then, it is added to water, extracted three times with ethyl acetate, washed neutral, dried on sodium sulfate, concentrated by evaporation in a vacuum and chromatographed on silica gel with hexane/ethyl acetate. 3.52 g of 9-[4-(5-chloropentyloxy)-phenyl]-8-phenyl-6,7-dihydro-5H-benzocycloheptene is obtained as crystals with a melting point of 118–120° C.

b) 9-[4-(5-Iodopentyloxy)-phenyl]-8-phenyl-6,7-dihydro-5H-benzocycloheptene A solution of 3.32 g of 9-[4-(5-chloropentyloxy)-phenyl]-8-phenyl-6,7-dihydro-5H-benzocycloheptene in 120 ml of ethylmethylketone is stirred with 4.5 g of sodium iodide for 9.5 hours at a bath temperature of 100° C. Then, it is added to water, extracted three times with ethyl acetate, washed neutral, dried on sodium sulfate and concentrated by evaporation in a vacuum. 4.02 g of 9-[4-(5-iodopentyloxy)-phenyl]-8-phenyl-6,7-dihydro-5H-benzocycloheptene is obtained as crystals with a melting point of 104–106° C.

c) (4,4,5,5,5-Pentafluoropentyl)-{5-[4-(6-phenyl-8,9-dihydro-7H-benzocyclohepten-5-yl)-phenoxy]-pentyl}-sulfide A solution of 2.35 g of 4,4,5,5,5-pentafluoropentylthioacetate in 12 ml of methanol is stirred with 1.88 ml of a 30% methanolic sodium methylate solution at room temperature for 0.5 hour. This solution is added in drops to a suspension of 4.0 g of 9-[4-(5-iodopentyloxy)-phenyl]-8-phenyl-6,7-dihydro-5H-benzocycloheptene in 44 ml of methanol and 44 ml of diethyl ether, and it is stirred for 6 hours at room temperature. Then, the methanol is concentrated by evaporation in a vacuum, added to water, extracted three times with ethyl acetate, washed neutral, dried on sodium sulfate and concentrated by evaporation in a vacuum. 4.5 g (4,4,5,5,5-pentafluoropentyl)-{5-[4-(6-phenyl-8,9-dihydro-7H-benzocyclohepten-5-yl)-phenoxy]-pentyl}-sulfide is obtained as crystals with a melting point of 84–85° C.

Example 2

(4,4,5,5,5-Pentafluoropentyl)-{5-[4-(6-phenyl-8,9-dihydro-7H-benzocyclohepten-5-yl)-phenoxy]-pentyl}-sulfoxide A solution of 4.4 g of (4,4,5,5,5-pentafluoropentyl)-{5-[4-(6-phenyl-8,9-dihydro-7H-benzocyclohepten-5-yl)-phenoxy]-pentyl}-sulfide in 130 ml of methanol is mixed at room temperature with 7.1 ml of water and 1.86 g of sodium periodate, and it is stirred for 24 hours. then, it is evaporated to the dry state in a vacuum, taken up with dichloromethane/water, washed with water, dried on sodium sulfate and concentrated by evaporation in a vacuum and chromatographed on silica gel with dichloromethane/acetone. 3.6 g of (4,4,5,5,5-pentafluoropentyl)-{5-[4-(6-phenyl-8,9-dihydro-7H-benzocyclohepten-5-yl)-phenoxy]-pentyl}-sulfoxide is obtained as colorless crystals with a melting point of 114–116° C.

Methyl-[3-(4,4,5,5,5-pentafluoropentylthio)-propyl]-{2-[4-(6-phenyl-8,9-dihydro-7H-benzocyclohepten-5-yl)-phenoxy]-ethyl}-amine a) 9-[4-(2-Chloroethoxy)-phenyl]-8-phenyl-6,7-dihydro-5H-benzocycloheptene

A suspension of 3.0 g of 4-(6-phenyl-8,9-dihydro-7H-benzocyclohepten-5-yl)-phenol{Raymond McCague, Reiko Kuroda, Guy Leclerq, Susanna Stoessel, J. Med. Chem. (29) 10 1986 pp. 2053–2059} in 51 ml of acetonitrile is stirred wtih 1.68 g of potassium carbonate and 0.95 ml of 1-bromo-2-chloroethane for 28 hours at a bath temperature of 100° C. Then, it is added to water, extracted three times with ethyl acetate, washed neutral, dried on sodium sulfate, concentrated by evaporation in a vacuum and chromatographed on silica gel with hexane/ethyl acetate. 2.93 g of 9-[4-(2-chloroethoxy)-phenyl]-8-phenyl-6,7-dihydro-5H-benzocycloheptene is obtained as crystals with a melting point of 171–172° C.

b) 9-[4-(2-Iodoethoxy)-phenyl]-8-phenyl-6,7-dihydro-5H-benzocycloheptene

A solution of 2.73 g of 9-[4-(2-chloroethoxy)-phenyl]-8-phenyl-6,7-dihydro-5H-benzocycloheptene in 110 ml of ethylmethylketone is stirred with 4.11 g of sodium iodide for 28 hours at a bath temperature of 100° C. Then it is added to water, extracted three times with ethyl acetate, washed neutral, dried on sodium sulfate, concentrated by evaporation in a vacuum and chromatographed on silica gel with hexane/ethyl acetate. 2.60 g of 9-[4-(2-iodoethoxy)-phenyl]-8-phenyl-6,7-dihydro-5H-benzocycloheptene is obtained as crystals with a melting point of 154–156° C.

c) Methyl-{2-[4-(6-phenyl-8,9-dihydro-7H-benzocyclohepten-5-yl)-phenoxy]-ethyl}-amine A solution of 2.2 g of 9-[4-(2-iodoethoxy)-phenyl]-8-phenyl-6,7-dihydro-5H-benzocycloheptene in 55 ml of dimethylformamide and 1.1 ml of triethylamine is stirred with 4.4 ml of a 40% aqueous methylamine solution of 1 hour at a bath temperature of 80° C. Then, it is added to saturated common salt solution, extracted three times with ethyl acetate, washed neutral, dried on sodium sulfate, concentrated by evaporation in a vacuum and chromatographed on silica gel with hexane/ethyl acetate. 0.9 g of methyl-{2-[4-(6-phenyl-8,9-dihydro-7H-benzocyclohepten-5-yl)-phenoxy]-ethyl}-amine is obtained as crystals with a melting point of 165–167° C.

d) Methyl-[3-(4,4,5,5,5-pentafluoropentylthio)-
propyl]-{2-[4-(6-phenyl-8,9-dihydro-7H-
benzocyclohepten-5-yl)-phenoxy]-ethyl}-amine A solution of 0.9 g of methyl-{2-[4-(6-phenyl-8,9-dihydro-7H-benzocyclohepten-5-yl)-phenoxy]-ethyl}-amine and 0.4 g of potassium carbonate in 14 ml of dimethylformamide is mixed drop by drop with a solution of 1.0 g of 1-iodo-3-(4,4,5,5,5-pentafluoropentylthio)-propane in 2 ml of dimethylformamide, and it is stirred for 2 hours at a bath temperature of 80° C. Then, it is added to water, extracted three times with ethyl acetate, washed neutral, dried on sodium sulfate and concentrated by evaporation in a vacuum. 570 mg of methyl-[3-(4,4,5,5,5-pentafluoropentylthio)-propyl]-{2-[4-(6-phenyl-8,9-dihydro-7H-benzocyclohepten-5-yl)-phenoxy]-ethyl}-amine is obtained as an oil.

Example 4

Methyl-[3-(4,4,5,5,5-pentafluoropentylsulfinyl)-
propyl]-{2-[4-(6-phenyl-8,9-dihydro-7H-
benzocyclohepten-5-yl)-phenoxy]-ethyl}-amine Analogously to what is described in Example 2, 0.55 g of methyl-[3-(4,4,5,5,5-pentafluoropentylthio)-propyl]-{2-[4-(6-phenyl-8,9-dihydro-7H-benzocyclohepten-5-yl)-phenoxy]-ethyl}-amine is oxidized, and 334 mg of methyl-[3-(4,4,5,5,5-pentafluoropentylsulfinyl)-propyl]-{2-[4-(6-phenyl-8,9-dihydro-7H-benzocyclohepten-5-yl)-phenoxy]-ethyl}-amine is obtained as crystals with a melting point of 74–77° C.

Example 5

S-{5-[4-(6-Phenyl-8,9-dihydro-7H-
benzocyclohepten-5-yl)-phenoxy]-pentyl}-
thioacetate A solution of 8.0 g of 9-[4-(5-iodopentyloxy)-phenyl]-8-phenyl-6,7-dihydro-5H-benzocycloheptene in 170 ml of acetone is stirred with 5.36 g of potassium thioacetate for 2.5 hours at room temperature. then, it is added to water, extracted three times with ethyl acetate, washed neutral, dried on sodium sulfate, concentrated by evaporation in a vacuum and chromatographed on silica gel with hexane/ethyl acetate. 6.5 g of S-{5-[4-(6-phenyl-8,9-dihydro-7H-benzocyclohepten-5-yl)-phenoxy}-pentyl}-thioacetate is obtained as crystals with a melting point of 118–120° C.

Example 6

N-Butyl-N-methyl-2-{5-[4-(6-phenyl-8,9-dihydro-
7H-benzocyclohepten-5-yl)-phenoxy)-pentylthio}-
acetamide A solution of 1 g of S-{5-[4-(6-phenyl-8,9-dihydro-7H-benzocyclohepten-5-yl)-phenoxy]-pentyl}-thioacetate in 15 ml of methanol and 10 ml of tetrahydrofuran is stirred with 0.42 ml of a 30% methanolic sodium methylate solution for 0.5 hour at room temperature, and after 0.5 ml of 2-bromo-N-butyl-N-methyl-acetamine is added, it is stirred for another hour. Then, it is added to water, extracted three times with ethyl acetate, washed neutral, dried on sodium sulfate, concentrated by evaporation in a vacuum and chromatographed on silica gel with hexane/ethyl acetate. 593 mg of N-butyl-N-methyl-2-{5-[4-(6-phenyl-8,9-dihydro-7H-benzocyclohepten-5-yl)-phenoxy]-pentylthio}-acetamide is obtained as an oil.

Example 7

N-Butyl-N-methyl-2-{5-[4-(6-phenyl-8,9-dihydro-
7H-benzocyclohepten-5-yl)-phenoxy]-
pentanesulfinyl}-acetamide Analogously to what is described in Example 2, 0.4 g of n-butyl-N-methyl-2-{5-[4-(6-phenyl-8,9-dihydro-7H-benzocyclohepten-5-yl)-phenoxy]-pentylthio}-acetamide is oxidized, and 301 mg of N-butyl-N-methyl-2-{5-[4-(6-phenyl-8,9-dihydro-7H-benzocyclohepten-5-yl)-phenoxy]-pentanesulfinyl}-acetamide is obtained as crystals with a melting point of 120–121° C.

Example 8

5-{4-[5-(4,4,5,5,5-Pentafluoro-pentylthio)-
pentyloxy]-phenyl}-6-phenyl-8,9-dihydro-7H-
benzocyclohepten-2-ol a) 2-Benzyloxy-5-(4-methoxyphenyl)-6,7,8,9-
tetrahydro-benzocyclohepten-5-ol A suspension of 14.57 g of magnesium chips in 150 ml of diethyl ether is mixed drop by drop with a solution of 88 ml of 4-bromanisole in 100 ml of diethyl ether so that the reaction mixture is refluxed without external heat supply. After the addition is completed, it is allowed to cool to room temperature, and a solution of 35.2 g of 2-benzyloxy-6,7,8,9-tetrahydro-benzocyclohepten-5-one [Lal, B. et al., J. Med. Chem. (15) 1972 pp. 23–27] in 150 ml of diethyl ether is slowly added and stirred for another 4.5 hours at room temperature. Then, it is cooled to 0° C., and saturated ammonium chloride solution is added. Then, it is added to water, extracted three times with ethyl acetate, washed neutral, dried on sodium sulfate, concentrated by evaporation in a vacuum and chromatographed on silica gel with hexane/ethyl acetate. 37 g of 2-benzyloxy-5-(4-methoxyphenyl)-6,7,8,9-tetrahydro-benzocyclohepten-5-yl is obtained as crystals with a melting point of 112–114° C.

b) 2-Benzyloxy-5-(4-methoxyphenyl)-8,9-dihydro-
7H-benzocycloheptene

A suspension of 35.8 g of 2-benzyloxy-5-(4-methoxyphenyl)-6,7,8,9-tetrahydrobenzocyclohepten-5-ol in 1 l of methanol is stirred with 32 ml of concentrated hydrochloric acid for 3 hours at room temperature. Then, it is neutralized with sodium bicarbonate solution, concentrated by evaporation in a vacuum to 300 ml, added to water, extracted three times with ethyl acetate, washed neutral, dried on sodium sulfate and concentrated by evaporation in a vacuum. 34 g of 2-benzyloxy-5-(4-methoxyphenyl)-8,9-dihydro-7H-benzocycloheptene is obtained as crystals with a melting point of 76–78° C.

c) 2-Benzyloxy-6-bromo-5-(4-methoxyphenyl)-8,9-
dihydro-7H-benzocycloheptene

A solution of 34 g of 2-benzyloxy-5-(4-methoxyphenyl)-8,9-dihydro-7H-benzocycloheptene in 310 ml of dichloromethane is mixed at 0° C. in portions with 29 g of pyridinium hydrobromide perbromide for 1 hour, and it is stirred for 0.5 hour at 0° C. Then, 200 ml of an aqueous sodium hydrogen sulfite solution is added at 0° C., added to water, extracted twice with dichloromethane, washed with sodium bicarbonate and common salt solution, dried on sodium sulfate, concentrated by evaporation in a vacuum and chromatographed on silica gel with hexane/ethyl acetate. 35 g of 2-benzyloxy-6-bromo-5-94-methoxyphenyl)-8,9-dihydro-7H-benzocycloheptene is obtained as crystals with a melting point of 141–143° C.

d) 2-Benzyloxy-5-(4-methoxyphenyl)-6-phenyl-8,9-
dihydro-7H-benzocycloheptene

A suspension of 22.32 g of zinc chloride in 60 ml of tetrahydrofuran is mixed at room temperature with 91.2 ml of a 1.8 M phenyllithium solution within three minutes, and it is stirred for 0.5 hour at a bath temperature of 90° C. This solution is added to a solution of 3.16 g of tetrakistriphenylphosphine palladium (O) and 24 g of 2-benzyloxy-6-bromo-5-(4-methoxyphenyl)-8,9-dihydro-7H-benzocycloheptene in 144 ml of tetrahydrofuran, and it is stirred for another 3 hours at a bath temperature of 90° C. Then, it is added to 170 ml of a 1M hydrochloric acid, extracted three times with ethyl acetate, dried on sodium sulfate, concentrated by evaporation in a vacuum and absorptively precipitated with diethyl ether. 22.53 g of 2-benzyloxy-5-(4-methoxyphenyl)-6-phenyl-8,9-dihydro-7H-benzocycloheptene is obtained as crystals with a melting point of 163–164° C.

e) 5-(4-Methoxyphenyl)-6-phenyl-8,9-dihydro-7H-benzocyclohepten-2-ol

A solution of 21.16 g of 2-benzyloxy-5-(4-methoxyphenyl)-6-phenyl-8,9-dihydro-7H-benzocycloheptene in 900 ml of dichloromethane is stirred at 0° C. with 19 ml of N,N-dimethylaniline for 5 minutes, mixed in portions with 26.1 g of aluminum chloride and stirred for another 3 hours at 0° C. Then, it is mixed with 1 M hydrochloric acid, added to water, extracted three times with dichloromethane, washed neutral, dried on sodium sulfate, concentrated by evaporation in a vacuum and absorptively precipitated with hexane/diethyl ether. 17.4 g of 5-(4-methoxyphenyl)-6-phenyl-8,9-dihydro-7H-benzocyclohepten-2-ol is obtained as crystals with a melting point of 232–233° C.

f) 2-[5-(4-Methoxyphenyl)-6-phenyl-8,9-dihydro-7H-benzocyclohepten-2-yloxy]-tetrahydropyran A suspension of 15.8 g of 5-(4-methoxyphenyl)-6-phenyl-8,9-dihydro-7H-benzocyclohepten-2-ol in 150 ml of toluene is stirred with 15 ml of dihydropyran and 60 mg of para-toluenesulfonic acid-monohydrate for 18 hours at room temperature. Then, it is diluted with ethyl acetate, washed with sodium bicarbonate and common salt solution, dried on sodium sulfate and concentrated by evaporation in a vacuum. 19.7 g of 2-[5-(4-methoxyphenyl)-6-phenyl-8,9-dihydro-7H-benzocyclohepten-2-yloxy]-tetrahydropyran is obtained as crystals with a melting point of 131–133° C.

g) 4-[6-Phenyl-2-(tetrahydropyran-2-yloxy)-8,9-dihydro-7H-benzocyclohepten-5-yl]-phenol A solution of 19.7 g of 2-[5-(4-methoxyphenyl)-6-phenyl-8,9-dihydro-7H-benzocyclohepten-2-yloxy]-tetrahydropyran in 500 ml of dimethylformamide is stirred with 9.73 g of sodium methylthiolate for 6.5 hours at a bath temperature of 140° C. Then, it is added to water, extracted three times with ethyl acetate, washed neutral, dried on sodium sulfate, concentrated by evaporation in a vacuum and chromatographed on silica gel with hexane/ethyl acetate. 17.2 g of 4-[6-phenyl-2-(tetrahydropyran-2-yloxy)-8,9-dihydro-7H-benzocyclohepten-5-yl]-phenol is obtained as crystals with a melting point of 183–185° C.

h) 2-{5-[4-(5-Chloropentyloxy)-phenyl]-6-phenyl-8,9-dihydro-7H-benzocyclohepten-2-yloxy}-tetrahydropyran A solution of 6.0 g of 4-[6-phenyl-2-(tetrahydropyran-2-yloxy)-8,9-dihydroxy-7H-benzocyclohepten-5-yl]-phenol in 77 ml of acetonitrile is stirred with 2.55 g of potassium carbonate and 2.27 ml of 1-bromo-5-chloropentane for 9 hours at 90° C. Then, it is added to water, extracted three times with ethyl acetate, washed neutral, dried on sodium sulfate, concentrated by evaporation in a vacuum and chromatographed on silica gel with hexane/ethyl acetate. 6.9 g of 2-{5-[4-(5-chloropentyloxy)-phenyl]-6-phenyl-8,9-dihydro-7H-benzocyclohepten-2-yloxy}-tetrahydro-pyran is obtained as crystals with a melting point of 99–101° C.

i) 5-[4-(5-Chloropentyloxy)-phenyl]-6-phenyl-8,9-dihydro-7H-benzocyclohepten-2-ol A solution of 6.7 g of 2-{5-[4-(5-chloropentyloxy)-phenyl]-6-phenyl-8,9-dihydro-7H-benzocyclohepten-2-yloxy}-tetrahydropyran in 130 ml of methanol and 13 ml of water is stirred with 5.7 g of oxalic acid for 1 hour at a bath temperature of 100° C. Then, it is concentrated by evaporation in a vacuum to 50 ml, added to water, extracted three times with ethyl acetate, washed neutral, dried on sodium sulfate, evaporated to the dry state in a vacuum and recrystallized from ethyl acetate. 5.48 g of 5-[4-(5-chloropentyloxy)-phenyl]-6-phenyl-8,9-dihydro-7H-benzocyclohepten-2-ol is obtained as crystals with a melting point of 200–202° C.

j) 5-[4-(5-Iodopentyloxy)-phenyl]-6-phenyl-8,9-dihydro-7H-benzocyclohepten-2-ol A solution of 5.28 g of 5-[4-(5-chloropentyloxy)-phenyl]-6-phenyl-8,9-dihydro-7H-benzocyclohepten-2-yl in 185 ml of ethylmethylketone is stirred with 6.9 g of sodium iodide for 24 hours at a bath temperature of 100° C. Then, it is added to water, extracted three times with ethyl acetate, washed neutral, dried on sodium sulfate, concentrated by evaporation in a vacuum and crystallized from acetone/hexane. 5.86 g of 5-[4-(5-iodopentyloxy)-phenyl]-6-phenyl-8,9-dihydro-7H-benzocyclohepten-2-ol is obtained as crystals with a melting point of 192–193° C.

k) 5-{4-[5-(4,4,5,5,5-Pentafluoro-pentylthio)-pentyloxy]-phenyl}-6-phenyl-8,9-dihydro-7H-benzocyclohepten-2-ol A solution of 1.7 g of 4,4,5,5,5-pentafluoropentylthioacetate in 9 ml of methanol is stirred with 1.36 ml of a 30% methanolic sodium methyl solution at room temperature for 0.5 hour. This solution is added in drops to a suspension of 3 g of 5-[4-(5-iodopentyloxy)-phenyl]-6-phenyl-8,9-dihydro-7H-benzocyclohepten-2-ol in 35 ml of methanol and 35 ml of diethyl ether, and it is stirred for 4 hours at room temperature. Then, it is concentrated by evaporation in a vacuum to 15 ml, added to water, extracted three times with ethyl acetate, washed neutral, dried on sodium sulfate and evaporated to the dry state in a vacuum. 3.38 g of 5-{4-[5-(4,4,5,5,5-pentafluoro-pentylthio)-pentyloxy]-phenyl}6-phenyl-8,9-dihydro-7H-benzocyclohepten-2-ol is obtained as crystals with a melting point of 167–168° C.

Example 9=ZU 186 619

5-{4-[5-(4,4,5,5,5-Pentafluoro-pentanesulfinyl)-pentyloxy]-phenyl}-6-phenyl-8,9-dihydro-7H-benzocyclohepten-2-ol Analogously to what is described in Example 2, 2.38 g of 5-{4-[5-(4,4,5,5,5-pentafluoro-pentylthio)-pentyloxy]-phenyl}-6-phenyl-8,9-dihydro-7H-benzocyclohepten-2-ol is oxidized, and 2.2 g of 5-{4-[5-(4,4,5,5,5-pentafluoropentanesulfinyl)-pentyloxy]-phenyl}-6-phenyl-8,9-dihydro-7H-benzocyclohepten-2-ol is obtained as crystals with a melting point of 138–140° C.

Example 10

5-[4-(2-{Methyl-[3-(4,4,5,5,5-pentafluoro-pentanesulfinyl)-propyl]-amino}-ethoxy)-phenyl]-6-phenyl-8,9-dihydro-7H-benzocyclohepten-2-ol Analogously to what is described in Example 2, 0.8 g of 5-[4-(2-{methyl-[3-(4,4,5,5,5-pentafluoro-pentylthio)-propyl]amino}-ethoxy)-phenyl]-6-phenyl-8,9-dihydro-7H-benzocyclohepten-2-ol is oxidized, and 405 mg of 5-[4-(2-{methyl-[3-(4,4,5,5,5-pentafluoro-pentanesulfinyl)-propyl]-amino}-ethoxy)-phenyl]-6-phenyl-8,9-dihydro-7H-benzocyclohepten-2-ol is obtained as crystals with a melting point of 63–65° C.

Example 11

5-[4-(2-Methyl-[3-(4,4,5,5,5-pentafluoro-pentylthio)-propyl]-amino}-ethoxy)-phenyl]-6-phenyl-8,9-dihydro-7H-benzocyclohepten-2-ol a) 2-{5-[4-(2-Chloroethyloxy)-phenyl]-6-phenyl-8,9-dihydro-7H-benzocyclohepten-2-yloxy}-tetrahydropyran A solution of 6.0 g of 4-[6-phenyl-2-(tetrahydropyran-2-yloxy)-8,9-dihydro-7H-benzocyclohepten-5-yl]-phenol in 77 ml of acetonitrile is stirred with 2.55 g of potassium carbonate and 7.0 ml of 1-bromo-2-chloroethane for 48 hours at 90° C. Then, it is added to water, extracted three times with ethyl acetate, washed neutral, dried on sodium sulfate, concentrated by evaporation in a vacuum and chromatographed on silica gel with hexane/ethyl acetate. 6.7 g of 2-{5-[4-(2-chloroethyloxy)-phenyl]-6-phenyl-8,9-dihydro-7H-benzocyclohepten-2-yloxy)-tetrahydropyran is obtained as crystals with a melting point of 153–155° C.

b) 5-[4-(2-Chloroethyloxy)-phenyl]-6-phenyl-8,9-dihydro-7H-benzocyclohepten-2-ol A solution of 6.6 g of 2-{5-[4-(2-chloroethyloxy)-phenyl]-6-phenyl-8,9-dihydro-7H-benzocyclohepten-2-yloxy}-tetrahydropyran in 130 ml of methanol and 13 ml of water is stirred with 5.7 g of oxalic acid for 1 hour at a bath temperature of 100° C. Then, it is concentrated by evaporation in a vacuum to 50 ml, added to water, extracted three times with ethyl acetate, washed neutral, dried on sodium sulfate, evaporated to the dry state in a vacuum and recrystallized from ethyl acetate. 5.0 g of 5-[4-(2-chloroethyloxy)-phenyl)-6-phenyl-8,9-dihydro-7H-benzocyclohepten-2-ol is obtained as crystals with a melting point of 238–240° C.

c) 5-[4-(2-Iodoethyloxy)-phenyl]-6-phenyl-8,9-dihydro-7H-benzocyclohepten-2-ol

A solution of 5.0 g of 5-[4-(2-chloroethyloxy)-phenyl]-6-phenyl-8,9-dihydro-7H-benzocyclohepten-2-ol in 190 ml of ethylmethylketone is stirred with 7.24 g of sodium iodide for 28 hours at a bath temperature of 100° C. Then, it is added to water, extracted three times with ethyl acetate, washed neutral, dried on sodium sulfate, concentrated by evaporation in a vacuum and crystallized from acetone/hexane. 5.9 g of 5-[4-(2-iodoethyloxy)-phenyl]-6-phenyl-8,9-dihydro-7H-benzocyclohepten-2-ol is obtained as crystals with a melting point of 229–231° C.

d) 5-{4-[2-(Methylamino)-ethoxy]-phenyl}-6-phenyl-8,9-dihydro-7H-benzocyclohepten-2-ol A solution of 4.5 g of 5-[4-(2-iodoethyloxy)-phenyl]6-phenyl-8,9-dihydro-7H-benzocyclohepten-2-ol in 100 ml of 2-methoxyethanol is stirred with 7.2 ml of a 40% aqueous methylamine solution for 2 hours at a bath temperature of 100° C. Then, it is added to saturated common salt solution, extracted three times with ethyl acetate, washed neutral, dried on sodium sulfate, concentrated by evaporation in a vacuum and absorptively precipitated from ethyl acetate. 2.7 g of 5-{4-[2-(methylamino)-ethoxy]-phenyl}-6-phenyl-8,9-dihydro-7H-benzocyclohepten-2-ol is obtained as crystals with a melting point of 184–187° C.

e) 5-[4-(2-{Methyl-[3-(4,4,5,5,5-pentafluoro-pentylthio)-propyl)-amino}-ethoxy)-phenyl]-6-phenyl-8,9-dihydro-7H-benzocyclohepten-2-ol A solution of 1.7 g of 5-{4-[2-(methylamino)-ethoxy]-phenyl}-6-phenyl-8,9-dihydro-7H-benzocyclohepten-2-ol in 34 ml of 2-methoxyethanol is mixed drop by drop with 3.4 ml of 1-iodo-3-(4,4,5,5,5-pentafluoropentylthio)-propane, and it is stirred for 1 hour at a bath temperature of 140° C. Then, it is added to water, extracted three times with ethyl acetate, washed neutral, dried on sodium sulfate, concentrated by evaporation in a vacuum and crystallized from acetone/hexane. 1.1 g of 5-[4-(2-{methyl-[3-(4,4,5,5,5-pentafluoro-pentylthio)-propyl]amino}-ethoxy)-phenyl]-6-phenyl-8,9-dihydro-7H-benzocyclohepten-2-ol is obtained as crystals with a melting point of 40–42° C.

Example 12

N-Butyl-N-methyl-2-{5-[4-(2-hydroxy-6-phenyl-8,9-dihydroxy-7H-benzocyclohepten-5-yl)-phenoxy]-pentylthio}-acetamide a) 2-{5-[4-(5-Iodopentyloxy)-phenyl]-6-phenyl-8,9-dihydro-7H-benzocyclohepten-2-yloxy}-tetrahydropyran A solution of 1.25 g of 2-{5-[4-(5-chloropentyloxy)-phenyl]-6-phenyl-8,9-dihydro-7H-benzocyclohepten-2-yloxy}-tetrahydropyran in 40 ml of ethylmethylketone is stirred with 1.38 g of sodium iodide for 9 hours at a bath temperature of 100° C. Then, it is added to water, extracted three times with ethyl acetate, washed neutral, dried on sodium sulfate, concentrated by evaporation in a vacuum and chromatographed on silica gel with hexane/ethyl acetate. 0.7 g of 2-{5-[4-(5-iodopentyloxy)-phenyl]-6-phenyl-8,9-dihydro-7H-benzocyclohepten-2-yloxy}-tetrahydropyran is obtained as crystals with a melting point of 109–111° C.

b) S-{5-[4-(6-Phenyl-2-tetrahydropyranyloxy-8,9-dihydro-7H-benzocyclohepten-5-yl)-phenoxy]-pentyl}-thioacetate A solution of 0.7 g of 2-{5-[4-(5-iodopentyloxy)-phenyl]-6-phenyl-8,9-dihydro-7H-benzocyclohepten-2-yloxy}-tetrahydropyran in 15 ml of acetone is stirred with 392 mg of potassium thioacetate for 2 hours at room temperature. Then, it is added to water, extracted three times with ethyl acetate, washed neutral, dried on sodium sulfate, concentrated by evaporation in a vacuum and chromatographed on silica gel with hexane/ethyl acetate. 550 mg of S-{5-[4-(6-phenyl-2-tetrahydropyranyloxy-8,9-dihydro-7H-benzocyclohepten-5-yl)-phenoxy]-pentyl}-thioacetate is obtained as crystals with a melting point of 84–86° C.

c) N-Butyl-N-methyl-2-{5-[4-(6-phenyl-2-tetrahydropyranyloxy-8,9-dihydro-7H-benzocyclohepten-5-yl)-phenoxy]-pentylthio}-acetamide A solution of 0.5 g of S-{5-[4-(6-phenyl-2-tetrahydropyranoyloxy-8,9-dihydro-7H-benzocyclohepten- 5-yl)-phenoxy]-pentyl}-thioacetate in 8 ml of methanol and 5 ml of tetrahydrofuran is stirred with 0.2 ml of a 30% methanolic sodium methylate solution of 0.5 hour at room temperature, and after 0.25 ml of 2-bromo-N-butyl-N-methyl-acetamide is added, it is stirred for another hour. Then, it is added to water, extracted three times with ethyl acetate, washed neutral, dried on sodium sulfate, concentrated by evaporation in a vacuum and chromatographed on silica gel with hexane/ethyl acetate. 450 mg of N-butyl-N-methyl-2-{5-[4-(6-phenyl-2-tetrahydropyranyloxy-8,9-dihydro-7H-benzocyclohepten-5-yl)-phenoxy]-pentylthio}-acetamide is obtained as an oil.

d) N-Butyl-N-methyl-2-{5-[4-(2-hydroxy-6-phenyl-8,9-dihydro-7H-benzocyclohepten-5-yl)-phenoxy]-pentylthio}-acetamide A solution of 400 g of N-butyl-N-methyl-2-{5-[4-(6-phenyl-2-tetrahydropyranyloxy-8,9-dihydro-7H-benzocyclohepten-5-yl)-phenoxy]-pentylthio}-acetamide in 11 ml of methanol nd 1.1 ml of water is stirred with 0.4 g of oxalic acid for 1 hour at a bath temperature of 100° C. Then, it is added to water, extracted three times with ethyl acetate, washed neutral, dried on sodium sulfate, evaporated to the dry state in a vacuum and recrystallized from pentane. 360 mg of N-butyl-N-methyl-2-[5-[4-(2-hydroxy-6-phenyl-8,9-dihydro-7H-benzocyclohepten-5-yl)-phenoxy]-pentylthio}-acetamide is obtained as crystals with a melting point of 112–114° C.

Example 13

5-{4-[5-(4,4,5,5,5-Pentafluoro-pentanesulfonyl)-pentyloxy]-phenyl}-6-phenyl-8,9-dihydro-7H-benzocyclohepten-2-ol a) 2-{5-[4-(5-(4,4,5,5,5-Pentafluoro-pentanesulfonyl)-pentyloxy)-phenyl]-6-phenyl-8,9-dihydro-7H-benzocyclohepten-2-yloxy}-tetrahydropyran A suspension of 0.5 g of 4-[6-phenyl-2-(tetrahydropyran-2-yloxy)-8,9-dihydro-7H-benzocyclohepten-5-yl]-phenol (Example 8g) in 7 ml of tetrahydrofuran is stirred with 212.5 mg of potassium carbonate and 620 mg of 1-iodo-5-(4,4,5,5,5-pentafluoropentanesulfonyl)-pentane for 11 hours at a bath temperature of 100° C. Then, it is added to water, extracted three times with ethyl acetate, washed neutral, dried on sodium sulfate, concentrated by evaporation in a vacuum and chromatographed on silica gel with hexane/ethyl acetate. 770 mg of 2-{5-[4-(5-(4,4,5,5,5-pentafluoro-pentanesulfonyl)-pentyloxy)-phenyl]-6-phenyl-8,9-dihydro-7H-benzocyclohepten-2-yloxy}-tetrahydropyran is obtained as crystals with a melting point of 107–110° C.

b) 5-{4-[5-(4,4,5,5,5-Pentafluoro-pentanesulfonyl)-pentyloxy]-phenyl}-6-phenyl-8,9-dihydro-7H-benzocyclohepten-2-ol A solution of 0.7 g of 2-{5-[4-(5-(4,4,5,5,5-pentafluoro-pentanesulfonyl)-pentyloxy)-phenyl]-6-phenyl-8,9-dihydro-7H-benzocyclohepten-2-yloxy]-tetrahydropyran in 16 ml of methanol and 1.6 ml of water is stirred with 0.7 g of oxalic acid for 1 hour at a bath temperature of 100° C. Then, it is concentrated by evaporation in a vacuum to 50 ml k, added to water, extracted three times with ethyl acetate, washed neutral, dried on sodium sulfate, evaporated to the dry state in a vacuum and recrystallized from ethyl acetate. 0.46 g of 5-{4-[5-(4,4,5,5,5-pentafluoro-pentanesulfonyl)-pentyloxy]-phenyl}-6-phenyl-8,9-dihydro-7H-benzocyclohepten-2-ol is obtained as crystals with a melting point of 176–178° C.

Example 14

N-Butyl-N-methyl-2-{5-[4-(2-hydroxy-6-phenyl-8,9-dihydro-7H-benzocyclohepten-5-yl)-phenoxy]-pentanesulfinyl}-acetamide Analogously to what is described in Example 2, 210 mg of N-butyl-N-methyl-2-{5-[4-(2-hydroxy-6-phenyl-8,9-dihydro-7H-benzocyclohepten-5-yl)-phenoxy]-pentylthio)-acetamide (Example 12) is oxidized, and 132 mg of N-butyl-N-methyl-2-{5-[4-(2-hydroxy-6-phenyl-8,9-dihydro-7H-benzocyclohepten-5-yl)-phenoxy]-pentanesulfinyl}-acetamide is obtained as crystals with a melting point of 87–89° C.

Example 15

N-Butyl-2-[2-({2-[4-(2-hydroxy-6-phenyl-8,9-dihydro-7H-benzocyclohepten-5-yl)-phenoxy]-ethyl}-methyl-amino)-ethanesulfinyl]-N-methyl-acetamide a) 2-{5-[4-(2-Iodoethyloxy)-phenyl]-6-phenyl-8,9-dihydro-7H-benzocyclohepten-2-yloxy]-tetrahydropyran Analogously to what is described in Example 11c, a solution of 1.7 g of 2-{5-[4-(2-chloroethyloxy)-phenyl]-6-phenyl-8,9-dihydro-7H-benzocyclohepten-2-yloxy}{-tetrahydropyran (Example 11a) is iodized, and 2 g of 2-{5-[4-(2-iodoethyloxy)-phenyl]-6-phenyl-8,9-dihydro-7H-benzocyclohepten-2-yloxy}-tetrahydropyran is obtained as crystals with a melting point of 165–166° C.

b) 2-{5-{4-[2-(Methylamino)-ethoxy]-phenyl}-6-phenyl-8,9-dihydro-7H-benzocyclohepten-2-yloxy}-tetrahydropyran A solution of 2 g of 2-{5-[4-(2-iodoethyloxy)-phenyl]-6-phenyl-8,9-dihydro-7H-benzocyclohepten-2-yloxy}-tetrahydropyran in 45 m of 2-methoxyethanol is stirred with 3.2 ml of a 40% aqueous methylamine solution of 2 hours at a bath temperature of 100° C. Then, it is added to saturated sodium bicarbonate solution, extracted three times with ethyl acetate, washed neutral, dried on sodium sulfate and concentrated by evaporation in a vacuum. 1.65 g of 2-{5-{4-[2-(methylamino)-ethoxy]-phenyl}-6-phenyl-8,9-dihydro-7H-benzocyclohepten-2-yloxy}-tetrahydropyran is obtained as crystals with a melting point of 133–137° C.

c) N-Butyl-2-[2-({2-[4-(6-phenyl-2-tetrahydropyranyloxy-8,9-dihydro-7H-benzocyclohepten-5-yl)-phenoxy]-ethyl}-methyl-amino)-ethanesulfinyl]-N-methyl-acetamide A solution of 825 mg of 2-{5-{4-[2-(methylamino)-ethoxy]-phenyl}-6-phenyl-8,9-dihydro-7H-benzocyclohepten-2-yloxy}-tetrahydropyran in 20 ml of 2-methoxyethanol is stirred with 583 mg of N-butyl-2-iodoethanesulfinyl-N-methyl-acetamide for 3.5 hours at a bath temperature of 120° C. Then, it is added to common salt solution, extracted three times with ethyl acetate, washed neutral, dried on sodium sulfate, concentrated by evaporation in a vacuum and chromatographed on silica gel with dichloromethane/methanol. 0.72 g of N-butyl-2-(2-({2-[4-(6-phenyl-2-tetrahydropyranyloxy-8,9-dihydro-7H- benzocyclohepten-5-yl)-phenoxy]-ethyl}-methyl-amino)-ethanesulfinyl]-N-methyl-acetamide is obtained as foam.

d) N-Butyl-2-{2-({2-[4-(2-hydroxy-6-phenyl-8,9-dihydro-7H-benzocyclohepten-5-yl)-phenoxy]-ethyl }-methyl-amino)-ethanesulfinyl]-N-methyl-acetamide Analogously to what is described in 11b, 245 mg of N-butyl-2-[2-({2-[4-(2-hydroxy-6-phenyl-8,9-dihydro-7H-benzocyclohepten-5-yl)-phenoxy]-ethyl }-methyl-amino)-ethanesulfinyl]-N-methyl-acetamide is obtained as crystals with a melting point of 72–74° C. from 720 mg of N-butyl-2-[2-({2-[4-(6-phenyl-2-tetrahydropyranyloxy-8,9-dihydro-7H-benzocyclohepten-5-yl)-phenoxy]-ethyl}-methyl-amino)-ethanesulfinyl]-N-methyl-acetamide.

Example 16

N-Butyl-2-(2-({2-[4-(2-hydroxy-6-phenyl-8,9-dihydro-7H-benzocyclohepten-5-yl)-phenoxy]-ethyl}-methyl-amino)-ethanesulfonyl]-N-methyl-acetamide a) N-Butyl-2-[2-({2-[4-(6-phenyl-2-tetrahydropyranyloxy-8,9-dihydro-7H-benzocyclohepten-5-yl)-phenoxy]-ethyl}-methyl-amino)-ethanesulfonyl]-N-methyl-acetamide A solution of 825 mg of 2-{5-{4-[2-(methylamino)-ethoxy]-phenyl}-6-phenyl-8,9-dihydro-7H-benzocyclohepten-2-yloxy}-tetrahydropyran in 20 ml of 2-methoxyethanol is stirred with 607 mg of N-butyl-2-iodoethanesulfonyl-N-methyl-acetamide for 3.5 hours at a bath temperature of 120° C. Then, it is added to common salt solution, extracted three times with ethyl acetate, washed neutral, dried on sodium sulfate, concentrated by evaporation in a vacuum and chromatographed on silica gel with dichloromethane/methanol. 324 mg of N-butyl-2(2-({2-[4-(6-phenyl-2-tetrahydropyranyloxy-8,9-dihydro-7H-benzocyclohepten-5-yl)-phenoxy]-ethyl}-methyl-amino)-ethanesulfonyl]-N-methyl-acetamide is obtained as a foam.

b) N-Butyl-2-[2-({2-[4-(2-hydroxy-6-phenyl-8,9-dihydro-7H-benzocyclohepten-5-yl)-phenoxy]-ethyl}-methyl-\amino)-ethanesulfonyl]-N-methyl-acetamide Analogously to what is described in Example 11b, 231 mg of N-butyl-2-[2-({2-[4-(2-hydroxy-6-phenyl-8,9-dihydro-7H-benzocyclohepten-5-yl)-phenoxy)-ethyl}-methyl-amino)-ethanesulfonyl]-N-methyl-acetamide is obtained from 300 mg of N-butyl-2-[2-({2-[4-(6-phenyl-2-tetrahydropyranyloxy-8,9-dihydro-7H-benzocyclohepten-5-yl)-phenoxy]-ethyl}-methyl-amino)-ethanesulfonyl]-N-methyl-acetamide as crystals with a melting point of 57–60° C.

Example 17

6-(4-Hydroxy-phenyl)-5-{4-[5-(4,4,5,5,5-pentafluoro-pentanesulfonyl)-pentyloxy]-phenyl}-8,9-dihydro-7H-benzocyclohepten-2-ol a) 2-Benzyloxy-6-(4-tert-butyldimethylsilyloxyphenyl)-5-(4-methoxyphenyl)-8,9-dihydro-7H-benzocycloheptene A solution of 10 g of 2-benzyloxy-6-bromo-5-(4-methoxyphenyl)-8,9-dihydro-7H-benzocycloheptene (Example 8c) in 114 ml of toluene and 57 ml of ethanol is stirred with 5.81 g of [4-(tert-butyldimethylsilyloxy)-phenyl]-boric acid, 23 ml of aqueous 2 M-sodium carbonate solution and 246 mg of tetrakistriphenylphosphine palladium(O) for 1 hour at a bath temperature of +90° C. Then, it is diluted with ethyl acetate, washed twice with water and common salt solution, dried on sodium sulfate and concentrated by evaporation in a vacuum. 13 g of 2-benzyloxy-6-(4-tert-butyldimethylsilyloxyphenyl)-5-(4-methoxyphenyl)-8,9-dihydro-7H-benzocycloheptene is obtained.

b) 4-[2-Benzyloxy-5-(4-methoxyphenyl)-8,9-dihydro-7H-benzocyclohepten-6-yl]-phenol A suspension of 13 g of 2-benzyloxy-6-(4-tert-butyldimethylsilyloxyphenyl)-5-(4-methoxyphenyl)-8,9-dihydro-7H-benzocycloheptene in 235 ml of methanol is stirred with 7.25 ml of concentrated hydrochloric acid for 7.5 hours at a bath temperature of 50° C. Then, it is neutralized with sodium bicarbonate, concentrated by evaporation in a vacuum, added to water, extracted three times with ethyl acetate, washed with common salt solution, dried on sodium sulfate, concentrated by evaporation in a vacuum and recrystallized from methanol. 10.3 g of 4-[2-benzyloxy-5-(4-methoxyphenyl)-8,9-dihydro-7H-benzocyclohepten-6-yl]-phenol is obtained as crystals with a melting point of 173–175° C.

c) 5-(4-Methoxyphenyl)-6-(4-hydroxyphenyl)-8,9-dihydro-7H-benzocyclohepten-2-ol

A solution of 10.3 g of 4-[2-benzyloxy-5-(4-methoxyphenyl)-8,9-dihydro-7H-benzocyclohepten-6-yl]-phenol in 350 ml of dichloromethane is stirred at 0° C. with 8.76 ml of N,N-dimethylaniline for 5 minutes and stirred with 12.2 g of aluminum chloride for 4.5 hours at 0° C. Then, it is mixed at 0° C. with 2 M hydrochloric acid, added to water, extracted three times with dichloromethane, washed neutral, dried on sodium sulfate, concentrated by evaporation in a vacuum and absorptively precipitated with diethyl ether and a little dichloromethane. 7.8 g of 5-(4-methoxyphenyl)-6-(4-hydroxyphenyl)-8,9-dihydro-7H-benzocyclohepten-2-ol is obtained as crystals with a melting point of 250–252° C.

d) 2-[5-(4-Methoxyphenyl)-6-(4-tetrahydropyranyloxyphenyl)-8,9-dihydro-7H-benzocyclohepten-2-yloxy]-tetrahydropyran A solution of 7.8 g of 5-(4-methoxyphenyl)-6-(4-hydroxyphenyl)-8,9-dihydro-7H-benzocyclohepten-2-ol in 80 ml of toluene and 40 ml of tetrahydrofuran is stirred with 17.4 ml of dihydropyran and 71.4 mg of paratoluenesulfonic acid for 20 hours at room temperature. Then, it is diluted with ethyl acetate, washed with sodium bicarbonate and common salt solution, dried on sodium sulfate, concentrated by evaporation in a vacuum and absorptively precipitated with diethyl ether and a little ethyl acetate. 8.1 g of 2-[5-(4-methoxyphenyl)-6-(4-tetrahydropyranyloxyphenyl)-8,9-dihydro-7H-benzocyclohepten-2-yloxy]-tetrahydropyran is obtained as crystals with a melting point of 160–161° C.

e) 4-[2-Tetrahydropyranyloxy-6-(4-tetrahydropyranyloxyphenyl)-8,9-dihydro-7H-benzocyclohepten-5-yl]-phenol A solution of 8.0 g of 2-[5-(4-methoxyphenyl)-6-(4-tetrahydropyranyloxyphenyl)-8,9-dihydro-7H- benzocyclohepten-2-yloxy]-tetrahydropyran in 160 ml of dimethylformamide is stirred with 3.2 g of sodium methanethiolate for 7 hours at 140° C. Then, it is added to water, extracted three times with ethyl acetate, washed neutral, dried on sodium sulfate, concentrated by evaporation in a vacuum and absorptively precipitated with diethyl ether. 7.4 g of 4-[2-tetrahydropyranyloxy-6-(4-tetrahydropyranyloxyphenyl)-8,9-dihydro-7H-benzocyclohepten-5-yl]-phenol is obtained as crystals with a melting point of 182–183° C.

f) 2-{5-[4-(5-(4,4,5,5,5-Pentafluoro-pentanesulfonyl)-pentyloxy]-phenyl-6-(4-tetrahydropyranyloxyphenyl)-8,9-dihydro-7H-benzocyclohepten-2-yloxy}-tetrahydropyran A suspension of 1 g of -[2-tetrahydropyranyloxy-6-(4-tetrahydropyranyloxyphenyl)-8,9-dihydro-7H-benzocyclohepten-5-yl]-phenol in 14 ml of acetonitrile is refluxed with 342 mg of potassium carbonate and 1 g of 1-iodo-5-(4,4,5,5,5-pentafluoropentanesulfonyl)-pentane for 21 hours at a bath temperature of 100° C. Then, it is concentrated by evaporation in a vacuum, added to water, extracted three times with ethyl acetate, washed neutral, dried on sodium sulfate, concentrated by evaporation in a vacuum and recrystallized from diethyl ether. 1.6 g of 2-{5-[4-(5-(4,4,5,5,5-pentafluoro-pentanesulfonyl)-pentyloxy)-phenyl]-6-(4-tetrahydropyranyloxyphenyl)-8,9-dihydro-7H-benzocyclohepten-2-yloxy}-tetrahydropyran is obtained as crystals with a melting point of 108–110° C.

g) 6-(4-Hydroxy-phenyl)-5-{4-[5-(4,4,5,5,5-pentafluoro-pentanesulfonyl)-pentyloxy]-phenyl}-8,9-dihydro-7H-benzocyclohepten-2-ol A suspension of 1.5 g of 2-{5-[4-(5-(4,4,5,5,5-pentafluoro-pentanesulfonyl)-pentyloxy)-phenyl]-6-(4-tetrahydropyranyloxyphenyl)-8,9-dihydro-7H-benzocyclohepten-2-yloxy}-tetrahydropyran in 34 ml of methanol as well as 3.4 ml of water is stirred with 1.5 g of oxalic acid for 1 hour at 100° C. Then, it is added to water, extracted three times with ethyl acetate, washed neutral, dried on sodium sulfate, concentrated by evaporation in a vacuum and chromatographed with hexane/diethyl ether. 924 mg of 6-(4-hydroxy-phenyl)-5-{4-(5-(4,4,5,5,5-pentafluoro-pentanesulfonyl)-pentyloxy]-phenyl}-8,9-dihydro-7H-benzocyclohepten-2-ol is obtained as crystals with a melting point of 168–170° C.

Example 18

N-Butyl-2-{6-[4-(2-hydroxy-6-phenyl-8,9-dihydro-7H-benzocyclohepten-5-yl)-phenoxy]-hexanesulfinyl}-N-methyl-acetamide Analogously to what is described in Example 2, 0.4 g of N-butyl-2-{6-[4-(2-hydroxy-6-phenyl-8,9-dihydro-7H-benzocyclohepten-5-yl)-phenoxy]-hexylthio}-N-methyl-acetamide (Example 19) is oxidized, and 394 mg of N-butyl-2-{6-[4-(2-hydroxy-6-phenyl-8,9-dihydro-7H-benzocyclohepten-5-yl)-phenoxy]-hexanesulfinyl}-N-methyl-acetamide is obtained as crystals with a melting point of 72–73° C.

Example 19

N-Butyl-2-{6-(4-(2-hydroxy-6-phenyl-8,9-dihydro-7H-benzocyclohepten-5-yl)-phenoxy)-hexylthio}-N-methyl-acetamide a) 2-{5-[4-(6-Chlorohexyloxy)-phenyl]-6-phenyl-8,9-dihydro-7H-benzocyclohepten-2-yloxy}-tetrahydropyran Analogously to what is described in Example 8h, 1.2 g of 4-[6-phenyl-2-(tetrahydropyran-2-yloxy)-8,9-dihydro-7H-benzocyclohepten-5-yl]-phenol (Example 8g) is alkylated with 0.52 ml of 1-bromo-6-chlorohexane, and 1.1 g of 2-{5-(4-(6-chlorohexyloxy)-phenyl]-6-phenyl-8,9-dihydro-7H-benzocyclohepten-2-yloxy}-tetrahydropyran is obtained as crystals with a melting point of 84–86° C.

b) 2-{5-[4-(6-Iodohexyloxy)-phenyl]-6-phenyl-8,9-dihydro-7H-benzocyclohepten-2-yloxy}-tetrahydropyran Analogously to what is described in Example 12a, 1 g of 2-{5-[4-(6-chlorohexyloxy)-phenyl]-6-phenyl-8,9-dihydro-7H-benzocyclohepten-2-yloxy}-tetrahydropyran is substituted with 1.07 g of sodium iodide, and 1.1 g of 2-{5-[4-(6-iodohexyloxy)-phenyl]-6-phenyl-8,9-dihydro-7H-benzocyclohepten-2-yloxy}-tetrahydropyran is obtained as crystals with a melting point of 108–110° C.

c) S-{6-[4-(6-Phenyl-2-tetrahydropyranyloxy-8,9-dihydro-7H-benzocyclohepten-5-yl)-phenoxy]-hexyl}-thioacetate Analogously to what is described in Example 12b, 1 g of 2-{5-[4-(6-iodohexyloxy)-phenyl]-6-phenyl-8,9-dihydro-7H-benzocyclohepten-2-yloxy}-tetrahydropyran is thioacetylated with 549 mg of potassium thioacetate, and 916 mg of S-{6-[4-(6-phenyl-2-tetrahydropyranyloxy-8,9-dihydro-7H-benzocyclohepten-5-yl)-phenoxy]-hexyl}-thioacetate is obtained as crystals with a melting point of 98–100° C.

d) N-Butyl-N-methyl-2-{6-[4-(6-phenyl-2-tetrahydropyranyloxy-8,9-dihydro-7H-benzocyclohepten-5-yl)-phenoxy]-hexylthio}-acetamide Analogously to what is described in Example 12c, 0.8 g of S-{6-[4-(6-phenyl-2-tetrahydropyranyloxy-8,9-dihydro-7H-benzocyclohepten-5-yl)-phenoxy]-hexyl}-thioacetate is reacted with 0.31 g of 2-bromo-N-butyl-N-methyl-acetamide to 632 mg of N-butyl-N-methyl-2-[6-[4-(6-phenyl-2-tetrahydropyranyloxy-8,9-dihydro-7H-benzocyclohepten-5-yl)-phenoxy]-hexylthio}-acetamide.

e) N-Butyl-2-{6-[4-(2-hydroxy-6-phenyl-8,9-dihydro-7H-benzocyclohepten-5-yl)-phenoxy]-hexylthio}-N-methyl-acetamide Analogously to what is described in Example 12d, 0.6 g of N-butyl-N-methyl-2-{6-[4-(6-phenyl-2-tetrahydropyranyloxy-8,9-dihydro-7H-benzocyclohepten-5-yl)-phenoxy]-hexylthio}-acetamide is reacted with 0.6 g of oxalic acid to 520 mg of N-butyl-2-{6-[4-(2-hydroxy-6-phenyl-8,9-dihydro-7H-benzocyclohepten-5-yl)-phenoxy]-hexylthio}-N-methyl-acetamide as crystals with a melting point of 103–105° C.

Example 20

6-(4-Hydroxy-phenyl)-5-{4-[5-(4,4,5,5,5-pentafluoropentylthio)-pentyloxy]-phenyl}-8,9-dihydro-7H-benzocyclohepten-2-ol a) 2-{5-[4-(5-Chloropentyloxy)-phenyl]-6-(4-tetrahydropyranyloxyphenyl)-8,9-dihydro-7H-benzocyclohepten-2-yloxy}-tetrahydropyran Analogously to what is described in Example 8h, 2 g of 4-[2-tetrahydropyranyloxy-6-(4-tetrahydropyranyloxyphenyl)-8,9-dihydro-7H- benzocyclohepten-5-yl]-phenol (Example 17e) is alkylated with 0.61 ml of 1-bromo-5-chloropentane, and 2.4 g of 2-{5-[4-(5-chloropentyloxy)-phenyl]-6-(4-tetrahydropyranyloxyphenyl)-8,9-dihydro-7H-benzocyclohepten-2-yloxy}-tetrahydropyran is obtained as crystals with a melting point of 110–112° C.

b) 2-{5-[4-(5-Iodopentyloxy)-phenyl]-6-(4-tetrahydropyranyloxyphenyl)-8,9-dihydro-7H-benzocyclohepten-2-yloxy}-tetrahydropyran Analogously to what is described in Example 12a, 2.3 g of 2-{5-[4-(5-chloropentyloxy)-phenyl[-6-(4-tetrahydropyranyloxyphenyl)-8,9-dihydro-7H-benzocyclohepten-2-yloxy}-tetrahydropyran is substituted with 2.13 g of sodium iodide, and 2.6 g of 2-{5-[4-(5-iodopentyloxy)-phenyl]-6-(4-tetrahydropyranyloxyphenyl)-8,9-dihydro-7H-benzocyclohepten-2-yloxy}-tetrahydropyran is obtained.

c) 6-(4-Hydroxy-phenyl)-5-[4-(5-iodopentyloxy)-phenyl]-8,9-dihydro-7H-benzocyclohepten-2-ol Analogously to what is described in Example 12d, 2.6 g of 2-{5-[4-(5-iodopentyloxy)-phenyl]-6-(4-tetrahydropyranyloxyphenyl)-8,9-dihydro-7H-benzocyclohepten-2-yloxy)-tetrahydropyran is reacted with 2.6 g of oxalic acid, and 2 g of 6-(4-hydroxy-phenyl)-5-[4-(5-iodopentyloxy)-phenyl]-8,9-dihydro-7H-benzocyclohepten-2-ol is obtained as crystals with a melting point of 202–204° C.

d) 6-(4-Hydroxy-phenyl)-5-{4-[5-(4,4,5,5,5-pentafluoropentylthio)-pentyloxy]-phenyl}-8,9-dihydro-7H-benzocyclohepten-2-ol Analogously to what is described in Example 8k, 1.9 g of 6-(4-hydroxy-phenyl)-5-[4-(5-iodopentyloxy)-phenyl]-8,9-dihydro-7H-benzocyclohepten-2-ol is reacted with 1.7 g of 4,4,5,5,5-pentafluoropentylthioacetate. 1.4 g of 6-(4-hydroxy-phenyl)-5-{4-[5-(4,4,5,5,5-pentafluoropentylthio)-pentyloxy]-phenyl}-8,9-dihydro-7H-benzocyclohepten-2-ol is obtained as crystals with a melting point of 157–158° C.

Example 21

6-(4-Hydroxy-phenyl)-5-{4-[5-(4,4,5,5,5-pentafluoropentane-sulfinyl)-pentyloxy]-phenyl}-8,9-dihydro-7H-benzocyclohepten-2-ol Analogously to what is described in Example 2, 1.3 g of 6-(4-hydroxy-phenyl)-5-{4-[5-(4,4,5,5,5-pentafluoropentylthio)-pentyloxy]-phenyl}-8,9-dihydro-7H-benzocyclohepten-2-ol is oxidized, and 2.2 g of 6-(4-hydroxy-phenyl)-5-{4-[5-(4,4,5,5,5-pentafluoropentane-sulfinyl)-pentyloxy]-phenyl}-8,9-dihydro-7H-benzocyclohepten-2-ol is obtained a crystals with a melting point of 165–168° C.

Example 22

5-{4-[4-(4,4,5,5,5-Pentafluoro-pentylthio)-butyloxy]-phenyl}-6-phenyl-8,9-dihydro-7H-benzocyclohepten-2-ol a) 2-{5-[4-(4-Chloro-butyloxy)-phenyl]-6-phenyl-8,9-dihydro-7H-benzocyclohepten-2-yloxy}-tetrahydropyran 4.8 g of 4-[6-phenyl-2-(tetrahydropyran-2-yloxy)-8,9-dihydro-7H-benzocyclohepten-5-yl]-phenol (Example: 8g) is introduced into 50 ml of acetonitrile, mixed at room temperature with 2.04 g of potassium carbonate and 1.61 ml of 1-bromo-4-chlorobutane and stirred for 8 hours at 90° C. Base on an incomplete reaction, 20% of the amount of potassium carbonate and 1-bromo-4-chlorobutane that are used at the beginning are added again and heated for another 6 hours at 90° C. For working-up, the preparation is concentrated by evaporation in a vacuum, mixed with water, extracted three times with ethyl acetate, washed with saturated sodium chloride solution, dried on magnesium sulfate and concentrated by evaporation in a vacuum. The residue is purified on silica gel with a hexane-ethyl acetate gradient. 5.18 g of 2-[5-[4-(4-chloro-butyloxy)-phenyl]-6-phenyl-8,9-dihydro-7H-benzocyclohepten-2-yloxy}-tetrahydropyran is obtained.

b) 5-[4-(4-Chloro-butyloxy)-phenyl]-6-phenyl-8,9-dihydro-7H-benzocyclohepten-2-ol 5.15 g of 2-{5-[4-(4-chloro-butyloxy)-phenyl)-6-phenyl-8,9-dihydro-7H-benzocyclohepten-2-yloxy}-tetrahydropyran is suspended in 100 ml of methanol and 10 ml of water, mixed with 4.47 g of oxalic acid and stirred for 75 minutes at 100° C. The solvent is drawn off in half in a vacuum, the preparation is added to water, extracted three times with ethyl acetate, washed with saturated sodium chloride solution, dried on magnesium sulfate and concentrated by evaporation in a vacuum. Preparative column chromatography on silica gel with a hexane-ethyl acetate gradient yields 5.01 g of 5-[4-(4-chloro-butyloxy)-phenyl]-6-phenyl-8,9-dihydro-7H-benzocyclohepten-2-ol.

c) 5-[4-(4-Iodo-butyloxy)-phenyl]-6-phenyl-8,9-dihydro-7H-benzocyclohepten-2-ol 2.0 g of 5-[4-(4-chloro-butyloxy)-phenyl]-6-phenyl-8,9-dihydro-7H-benzocyclohepten-2-ol is introduced into 72 ml of ethylmethylketone, mixed with 2.70 g of sodium iodide and refluxed for 12 hours at 100° C. The cooled reaction mixture is concentrated by evaporation in a vacuum, mixed with water and extracted three times with ethyl acetate. The organic phase is then washed with sodium thiosulfate solution and saturated sodium chloride solution. Drying on magnesium sulfate and concentration by evaporation in a vacuum yields 2.14 g of 5-[4-(4-iodo-butyloxy)-phenyl]-6-phenyl-8,9-dihydro-7H-benzocyclohepten-2-ol, which is used without further purification in the next stage.

d) 5-{4-[4-(4,4,5,5,5-Pentafluoro-pentylthio)-butyloxy]-phenyl}-6-phenyl-8,9-dihydro-7H-benzocyclohepten-2-ol A solution of 1.22 g of 4,4,5,5,5-pentafluoropentylthioacetate in 6 ml of methanol is stirred with 0.98 ml of a 30% methanolic sodium methylate solution at room temperature for 0.5 hour. This solution is added in drops to a suspension of 2.1 g of 5-[4-(4-iodo-butyloxy)-phenyl]-6-phenyl-8,9-dihydro-7H-benzocyclohepten-2-ol in 25 ml of methanol and 25 ml of diethyl ether, and it is stirred for 4 hours at room temperature. Then, the reaction mixture is concentrated by evaporation in a vacuum, added to water, extracted three times with ethyl acetate, washed neutral, dried on magnesium sulfate and concentrated by evaporation in a vacuum. Column chromatographic separation on silica gel with a hexane/ethyl acetate gradient yields 1.84 g of 5-{4-[4-(4,4,5,5,5-pentafluoro-pentylthio)-butyloxy]-phenyl}-6-phenyl-8,9-dihydro-7H-benzocyclohepten-2-ol with a melting point of: 167° C.

Example 23

6-Phenyl-5-{4-[4-(pyridin-2-ylmethylthio)-butyloxy]-phenyl}-8,9-dihydro-7H-benzocyclohepten-2-ol 12.3 g of a 10% ethanolic 2-mercaptomethylpyridine solution is mixed at room temperature drop by drop with 1.67 ml of a 30% methanolic sodium methylate solution, and it is stirred for 15 more minutes. Then, the solution is added in drops to a suspension of 1.70 g of 5-[4-(4-iodo-butyloxy)-phenyl]-6-phenyl-8,9-dihydro-7H-benzocyclohepten-2-ol (Example: 22c) in 16 ml of methanol, and it is refluxed for 2 hours at a bath temperature of 80° C. Solvent is removed from the cooled reaction mixture, the residue is mixed with semisaturated sodium chloride solution, extracted three times with ethyl acetate, washed with saturated sodium chloride solution, dried on magnesium sulfate and concentrated by evaporation in a vacuum. Column chromatographic purification on silica gel with a hexane-ethyl acetate gradient yields 1.37 g of 6-phenyl-5-{4-[4-(pyridin-2-ylmethylthio)-butyloxy]-phenyl}-8,9-dihydro-7H-benzocyclohepten-2-ol with a melting point of: 155° C.

Example 24

6-Phenyl-5-{4-[5-(pyridin-2-ylmethylthio)-pentyloxy]-phenyl}-8,9-dihydro-7H-benzocyclohepten-2-ol 21.4 g of a 10% ethanolic 2-mercaptomethylpyridine solution is mixed at room temperature drop by drop with 2.91 ml of a 30% methanolic sodium methylate solution, and it is stirred for 15 more minutes. Then, the solution is added in drops to a suspension of 2.52 g of 5-[4-(5-chloropentyloxy)-phenyl]-6-phenyl-8,9-dihydro-7H-benzocyclohepten-2-ol (Example: 8i) and 1.03 g of sodium iodide in 29 ml of methanol, and it is refluxed for 2 hours at a bath temperature of 80° C. For working-up, the reaction mixture is allowed to reach room temperature, and the solvent is removed in a vacuum. The residue is mixed with semisaturated sodium chloride solution, extracted three times with ethyl acetate, washed with saturated sodium chloride solution, dried on mag sulfate and concentrated by evaporation in a vacuum. Recrystallization from ethyl acetate results in 2.15 g of 6-phenyl-5-{4-[5-(pyridin-2-ylmethylthio)-pentyloxy]-phenyl}-8,9-dihydro-7H-benzocyclohepten-2-ol with a melting point of: 159° C.

Example 25

6-Phenyl-5-{4-[6-(pyridin-2-ylmethylthio)-hexyloxy]-phenyl}-8,9-dihydro-7H-benzocyclohepten-2-ol 16.8 g of a 10% ethanolic 2-mercaptomethylpyridine solution is mixed at room temperature drop by drop with 2.30 ml of a 30% methanolic sodium methylate solution, and it is stirred for 15 more minutes. Then, the solution is added in drops to a suspension of 2.05 g of 5-[4-(6-chlorohexyloxy)-phenyl]-6-phenyl-8,9-dihydro-7H-benzocyclohepten-2-ol (Example: 28a) and 812 mg of sodium iodide in 22 ml of methanol, and it is refluxed for 2 hours at a bath temperature of 80° C. For working-up, the reaction mixture is allowed to reach room temperature, and the solvent is removed in a vacuum. The residue is mixed with semisaturated sodium chloride solution, extracted three times with ethyl acetate, washed with saturated common salt solution, dried on magnesium sulfate and concentrated by evaporation in a vacuum. Recrystallization from ethyl acetate results in 1.63 g of 6-phenyl-5-{4-[6-(pyridin-2-ylmethylthio)-hexyloxy]-phenyl}-8,9-dihydro-7H-benzocyclohepten-2-ol with a melting point of: 127° C.

Example 26

5-{4-[4-(4,4,5,5,5-Pentafluoro-pentanesulfinyl)-butyloxy]-phenyl}-6-phenyl-8,9-dihydro-7H-benzocyclohepten-2-ol 1.41 g of 5-{4-[4-(4,4,5,5,5-pentafluoro-pentylthio)-butyloxy]-phenyl}-6-phenyl-8,9-dihydro-7H-benzocyclohepten-2-ol (Example: 22d) is suspended in 40 ml of methanol and 2.32 ml of water, mixed with 550 mg of sodium periodate and stirred for 12 hours at room temperature. Then, the methanol is drawn off in a vacuum, the residue is added to water, extracted three times with ethyl acetate, washed with saturated sodium chloride solution, dried on magnesium sulfate and concentrated by evaporation in a vacuum. Trituration of the crude product with hexane results in 1.39 g of 5-{4-[4-(4,4,5,5,5-pentafluoro-pentanesulfinyl)-butyloxy]-phenyl}-6-phenyl-8,9-dihydro-7H-benzocyclohepten-2-ol with a melting point of: 155° C.

Example 27

6-Phenyl-5-{4-[4-(pyridin-2-ylmethanesulfinyl)-butyloxy]-phenyl}-8,9-dihydro-7H-benzocyclohepten-2-ol 990 mg of 6-phenyl-5-{4-[4-(pyridin-2-ylmethylthio)-butyloxy]-phenyl}-8,9-dihydro-7H-benzocyclohepten-2-ol (Example: 23) is suspended in 3.2 ml of methanol and 1.85 ml of water, mixed with 440 mg of sodium periodate and stirred overnight at room temperature. On the following day, the preparation is heated for 75 minutes to 50° C. For working-up, the solvent is removed in a vacuum, the residue is mixed with water, extracted three times with ethyl acetate, washed with saturated sodium chloride solution, dried on magnesium sulfate and concentrated by evaporation in a vacuum. Purification of the crude product on silica gel with a methylene chloride-methanol gradient yields 612 mg of 6-phenyl-5-{4-[4-(pyridin-2-ylmethanesulfinyl)-butyloxy]-phenyl}-8,9-dihydro-7H-benzocyclohepten-2-ol with a melting point of: 162° C.

Example 28

5-{4-[6-(4,4,5,5,5-Pentafluoro-pentylthio)-hexyloxy}-phenyl}-6-phenyl-8,9-dihydro-7H-benzocyclohepten-2-ol a) 5-[4-(6-Chloro-hexyloxy)-phenyl]-6-phenyl-8,9-dihydro-7H-benzocyclohepten-2-ol 5.42 g of 2-{5-[4-(6-chloro-hexyloxy)-phenyl]-6-phenyl-8,9-dihydro-7H-benzocyclohepten-2-yloxy}-tetrahydropyran (Example: 19a) is dissolved in 100 ml of tetrahydrofuran and 10 ml of water, mixed with 4.674 g of oxalic acid and stirred for 75 minutes at a bath temperature of 100° C. Then, the reaction mixture is cooled to room temperature, and the solvent is removed in a vacuum. The residue is mixed with water, extracted three times with ethyl acetate, washed neutral, dried on magnesium sulfate and concentrated by evaporation in a vacuum. Column chromatographic separation on silica gel with a hexane-ethyl acetate gradient results in 4.17 g of 5-[4-(6-chloro-hexyloxy)-phenyl]-6-phenyl-8,9-dihydro-7H-benzocyclohepten-2-ol with a melting point of: 193° C.

b) 5-[4-(6-Iodo-hexyloxy)-phenyl]-6-phenyl-8,9-dihydro-7H-benzocyclohepten-2-ol 2.05 g of 5-[4-(6-chloro-hexyloxy)-phenyl]-6-phenyl-8,9-dihydro-7H-benzocyclohepten-2-ol is introduced into 70 ml of ethylmethylketone, mixed with 2.60 g of sodium iodide and stirred for 12 hours at a bath temperature of 100° C. The cooled reaction mixture is concentrated by evaporation in a vacuum, mixed with water and extracted three times with ethyl acetate. The organic phase is then washed with sodium thiosulfate solution and saturated sodium chloride solution.

Drying on magnesium sulfate and concentration by evaporation in a vacuum yields 2.50 g of 5-[4-(6-iodo-hexyloxy)-phenyl]-6-phenyl-8,9-dihydro-7H-benzocyclohepten-2-ol, which is used without further purification in the next stage.

c) 5-{4-[6-(4,4,5,5,5-Pentafluoro-pentylthio)-hexyloxy]-phenyl}-6-phenyl-8,9-dihydro-7H-benzocyclohepten-2-ol A solution of 1.37 g of 4,4,5,5,5-pentafluoropentylthioacetate in 6 ml of methanol is stirred with 1.1 ml of a 30% methanolic sodium methylate solution at room temperature for 0.5 hour. This solution is added in drops to a suspension of 2.48 g of 5-[4-(6-iodo-hexyloxy)-phenyl)-6-phenyl-8,9-dihydro-7H-benzocyclohepten-2-ol in 25 ml of methanol and 25 ml of diethyl ether, and it is stirred for 4 hours at room temperature. Then, the preparation is concentrated by evaporation in a vacuum, added to water, extracted three times with ethyl acetate, washed neutral, dried on magnesium sulfate and concentrated by evaporation in a vacuum. Recrystallization of the crude product from hexane/diethyl ether yields 2.44 g of 5-{4-[6-(4,4,5,5,5-pentafluoro-pentylthio)-hexyloxy]-phenyl}-6-phenyl-8,9-dihydro-7H-benzocyclohepten-2-ol with a melting point of: 166° C.

Example 29

5-{4-[6-(4,4,5,5,5-Pentafluoro-pentanesulfinyl)-hexyloxy]-phenyl}-6-phenyl-8,9-dihydro-7H-benzocyclohepten-2-ol 2.1 g of 5-{4-[6-(4,4,5,5,5-pentafluoro-pentylthio)-hexyloxy]-phenyl}-6-phenyl-8,9-dihydro-7H-benzocyclohepten-2-ol (Example: 28c) is introduced into 56 ml of methanol and 3.3 ml of water, mixed with 782 mg of sodium periodate and stirred for 12 hours at room temperature. Then, the methanol is drawn off in a vacuum, the residue is added to water, extracted three times with ethyl acetate, washed with saturated sodium chloride solution, dried on magnesium sulfate and concentrated by evaporation in a vacuum. 2.13 g of 5-{4-[6-(4,4,5,5,5-pentafluoro-pentanesulfinyl)-hexyloxy]-phenyl}-6-phenyl-8,9-dihydro-7H-benzocyclohepten-2-ol with a melting point of: 121° C. is obtained.

Example 30

6-Phenyl-5-{4-[6-(pyridin-2-ylmethanesulfinyl)-hexyloxy]-phenyl}-8,9-dihydro-7H-benzocyclohepten-2-ol 1.30 g of 6-phenyl-5-{4-[6-(pyridin-2-ylmethylthio)-hexyloxy]-phenyl}-8,9-dihydro-7H-benzocyclohepten-2-ol (Example: 25) is introduced into 40 ml of methanol and 2.3 ml of water, mixed with 550 mg of sodium periodate and stirred overnight at room temperature. On the following day, it is heated for 6 hours to 40° C., and stirred again overnight at room temperature. Then, the methanol is drawn off in a vacuum, the residue is mixed with water, extracted three times with ethyl acetate, washed with saturated sodium chloride solution, dried on magnesium sulfate and concentrated by evaporation in a vacuum. Column chromatographic separation on silica gel with a methylene chloride-methanol gradient yields 464 mg of 6-phenyl-5-{4-[6-(pyridin-2-ylmethanesulfinyl)-hexyloxy]-phenyl}-8,9-dihydro-7H-benzocyclohepten-2-ol with a melting point of: 80° C.

Example 31

6-Phenyl-5-{4-[5-(pyridin-2-ylmethanesulfinyl)-pentyloxy]-phenyl}-8,9-dihydro-7H-benzocyclohepten-2-ol 1.86 g of 6-phenyl-5-{4-[5-(pyridin-2-ylmethylthio)-pentyloxy]-phenyl}-8,9-dihydro-7H-benzocyclohepten-2-ol (Example: 24) is introduced into 58 ml of methanol and 3.4 ml of water, mixed with 805 mg of sodium periodate, stirred overnight at room temperature and on the following day for 6 hours at 40° C. Then, the methanol is drawn off in a vacuum, the residue is mixed with water, extracted three times with ethyl acetate, washed with saturated sodium chloride solution, dried on magnesium sulfate and concentrated by evaporation in a vacuum. 2.97 g of crude product, which is preferably by column chromatography with a methylene chloride/methanol gradient is obtained. Recrystallization from methylene chloride/ether yields 635 mg of 6-phenyl-5-{4-]5-(pyridin-2-ylmethanesulfinyl)-pentyloxy]-phenyl}-8,9-dihydro-7H-benzocyclohepten-2-ol with a melting point of: 176° C.

Example 32

5-{4-[5-(Furan-2-ylmethylthio)-pentyloxy]-phenyl}-6-phenyl-8,9-dihydro-7H-benzocyclohepten-2-ol 0.6 ml of furfurylmercaptan in 2 ml of methanol is mixed at room temperature drop by drop with 1.1 ml of a 30% methanolic sodium methylate solution, and it is stirred for 15 more minutes. Then, the solution is added in drops to a suspension of 1.08 g of 5-[4-(5-iodopentyloxy)-phenyl]-6-phenyl-8,9-dihydro-7H-benzocyclohepten-2-ol (Example: 8j) in 10 ml of methanol, and it is heated for 2 hours to a bath temperature of 80° C. For working-up, the reaction mixture is allowed to reach room temperature, stirred into semisaturated sodium chloride solution, extracted three times with ethyl acetate, washed with saturated sodium chloride solution, dried on magnesium sulfate and concentrated by evaporation in a vacuum. Recrystallization from hexane results in 920 mg of 5-{4-[5-(furan-2-ylmethylthio)-pentyloxy]-phenyl}-6-phenyl-8,9-dihydro-7H-benzocyclohepten-2-ol with a melting point of: 171° C.

Example 33

6-Phenyl-5-{4-[5-(thien-2-ylmethylthio)-pentyloxy]-phenyl}-8,9-dihydro-7H-benzocyclohepten-2-ol 0.24 ml of 2-thienylmethylmercaptan is dissolved in 1 ml of methanol and mixed drop by drop at room temperature with 0.5 ml of 30% methanolic sodium methylate solution. It is stirred for 15 more minutes, before this solution is added to a suspension of 524 mg of 5-[4-(5-iodopentyloxy)-phenyl]-6-phenyl-8,9-dihydro-7H-benzocyclohepten-2-ol (Example: 8j) in 5 ml of methanol, and it is heated for 2 hours to a bath temperature of 80° C. The reaction mixture that is cooled to room temperature is added to semisaturated sodium chloride solution, extracted three times with ethyl acetate, dried on magnesium sulfate and concentrated by evaporation in a vacuum. Recrystallization from hexane yields 451 mg of 6-phenyl-5-{4-[5-(thien-2-ylmethylthio)-pentyloxy]-phenyl}-8,9-dihydro-7H-benzocyclohepten-2-ol with a melting point of: 178° C.

Examples 34 and 35

5-{4-[5-(Furan-2-ylmethanesulfinyl)-pentyloxy]-phenyl}-6-phenyl-8,9-dihydro-7H-benzocyclohepten-2-ol and 5-{4-[5-(furan-2-ylmethanesulfonyl)-pentyloxy]-phenyl}-6-phenyl-8,9-dihydro-7H-benzocyclohepten-2-ol 510 mg of 5-{4-[5-(furan-2-ylmethylthio)-pentyloxy]-phenyl}-6-phenyl-8,9-dihydro-7H-benzocyclohepten-2-ol (Example; 32) is dissolved in 16 ml of methanol and 0.95 ml of water, mixed with 225 mg of sodium periodate and stirred overnight at room temperature. On the following day, 55 mg of sodium periodate is again added and stirred for 1 hour at 50° C. The cooled reaction mixture is added to semisaturated sodium chloride solution, extracted three times with ethyl acetate, washed with saturated sodium chloride solution, dried on sodium sulfate and concentrated by evaporation in a vacuum. Column chromatographic purification on silica gel with a hexane-ethyl acetate gradient results in 498 mg of 5-{4-[5-(furan-2-ylmethanesulfinyl)-pentyloxy]-phenyl}-6-phenyl-8,9-dihydro-7H-benzocyclohepten-2-ol with a melting point of: 168° C. and 16 mg of 5-{4-(4-(furan-2-ylmethanesulfonyl)-pentyloxy]-phenyl}-6-phenyl-8,9-dihydro-7H-benzocyclohepten-2-ol with a melting point of: 186° C.

Examples 36 and 37

6-Phenyl-5-{4-[5-(thien-2-ylmethanesulfonyl)-pentyloxy]-phenyl}-8,9-dihydro-7H-benzocyclohepten-2-ol and 6-phenyl-5-{4-[5-(thien-2-ylmethanesulfinyl)-pentyloxy]-phenyl}-8,9-dihydro-7H-benzocyclohepten-2-ol 386 mg of 6-phenyl-5-{4-[5-(thien-2-ylmethylthio)-pentyloxy]-phenyl}-8,9-dihydro-7H-benzocyclohepten-2-ol (Example: 33) is reacted analogously to Examples 34/35. After chromatographic purification on silica gel with a hexane-ethyl acetate gradient, 28 mg of 6-phenyl-5-{4-[5-(thien-2-ylmethanesulfonyl)-pentyloxy]-phenyl}-8,9-dihydro-7H-benzocyclohepten-2-yl with a melting point of: 212° C. and 312 mg of 6-phenyl-5-{4-[5-(thien-2-ylmethanesulfinyl)-pentyloxy]-phenyl}-8,9-dihydro-7H-benzocyclohepten-2-ol with a melting point of: 174–177° C. are obtained.

Example 38

5-{4-[5-(3,3,4,4,5,5,5-Heptafluoro-pentylthio)-pentyloxy]-phenyl}-6-phenyl-8,9-dihydro-7H-benzocyclohepten-2-ol a) (3,3,4,4,5,5,5-Heptafluoro-pentyl)-(5-{4-[6-phenyl-2-(tetrahydropyran-2-yloxy)-8,9-dihydro-7H-benzocyclohepten-5-yl}-phenoxy}-pentyl)-sulfide 404 mg of S-(5-{4-[6-phenyl-2-tetrahydropyran-2-yloxy)-8,9-dihydro-7H-benzocyclohepten-5-yl]-phenoxy}-pentyl)-thioacetate (Example: 12b) in 1 ml of methanol is mixed at room temperature drop by drop with 0.14 ml of 30% methanolic sodium methylate solution. It is stirred for 30 more minutes at room temperature before 187 mg of heptafluoro-5-iodopentane in 4 ml of methanol is added in drops. After 90 minutes of stirring at room temperature, the preparation is added to semisaturated sodium chloride solution, extracted three times with ethyl acetate, dried on magnesium sulfate and concentrated by evaporation in a vacuum. Column chromatographic purification of the residue on silica gel with a hexane-ethyl acetate gradient yields 120 mg of (3,3,4,4,5,5,5-heptafluoro-pentyl)-(5-{4-[6-phenyl-2-(tetrahydropyran-2-yloxy)-8,9-dihydro-7H-benzocyclohepten-5-yl]-phenoxy}-pentyl)-sulfide.

b) 5-{4-[5-(3,3,4,4,5,5,5-Heptafluoro-pentylthio)-pentyloxy]-phenyl}-6-phenyl-8,9-dihydro-7H-benzocyclohepten-2-ol 110 mg of (3,3,4,4,5,5,5-heptafluoro-pentyl)-(5-{4-[6-phenyl-2-(tetrahydropyran-2-yloxy)-8,9-dihydro-7H-benzocyclohepten-5-yl]-phenoxy}-pentyl)-sulfide is dissolved in 2.5 ml of methanol and 0.25 ml of water, mixed with 100 mg of oxalic added in drops and stirred for 2 hours at 50° C. The cooled reaction mixture is mixed with about 5 ml of water and stirred for 30 minutes. The deposited precipitation is suctioned off, thoroughly rewashed and dried in a vacuum. 86 mg of 5-{4-(5-(3,3,4,4,5,5,5-heptafluoro-penthylthio)-pentyloxy]-phenyl}-6-phenyl-8,9-dihydro-7H-benzocyclohepten-2-ol with a melting point of 156° C. is obtained.

Example 39

5-{4-[2-(2-Hydroxy-ethylamino)-ethoxy]-phenyl}-6-phenyl-8,9-dihydro-7H-benzocyclohepten-2-ol A solution of 1 g of 5-[4-(2-iodoethyloxy)-phenyl]-6-phenyl-8,9-dihydro-7H-benzocyclohepten-2-ol (Example 11c) in 10 ml of methanol is refluxed with 1.24 ml of 2-aminoethanol for 0.5 hour at a bath temperature of 160° C. Then, it is added to sodium bicarbonate solution, extracted three times with ethyl acetate/methanol (4/1), washed neutral, dried on sodium sulfate, concentrated by evaporation in a vacuum and recrystallized from ethyl acetate/methanol. 621 mg of 5-{4-[2-(2-hydroxy-ethylamino)-ethoxy]-phenyl}-6-phenyl-8,9-dihydro-7H-benzocyclohepten-2-ol is obtained as crystals with a melting point of 176–178° C.

Starting Material

1-Iodo-3-(4,4,5,5,5-pentafluoropentylthio)-propane 1-iodo-5-(4,4,5,5,5-pentafluoropentanesulfinyl)-pentane 1-iodo-5-(4,4,5,5,5-pentafluoropentanesulfonyl)-pentane N-butyl-2-iodoethanesulfinyl-N-methyl-acetamide Example 40

5-{4-[5-(4-Fluoro-butylthio)-pentyloxy]-phenyl}-6-phenyl-8,9-dihydro-7H-benzocyclohepten-2-ol a) (4-Fluoro-butyl)-(5-{4-[6-phenyl-2-(tetrahydropyran-2-yloxy)-8,9-dihydro-7H-benzocyclohepten-5-yl]-phenoxy}-pentyl)-sulfide 500 mg of S-(5-{4-[6-phenyl-2-(tetrahydropyran-2-yloxy)-8,9-dihydro-7H-benzocyclohepten-5-yl]-phenoxy}-pentyl)-thioacetate (Example: 12b) is dissolved in 5 ml of tetrahydrofuran and 7.4 ml of methanol and mixed at room temperature drop by drop with 0.2 ml of a 30% methanolic sodium methylate solution. After the addition has been completed, it is stirred for 30 more minutes at room temperature before 0.15 ml of 1-bromo-4-fluorobutane is added in drops at the same temperature. After 90 minutes, the reaction mixture is mixed with semisaturated sodium chloride solution, extracted three times with ethyl acetate, washed neutral, dried on magnesium sulfate and concentrated by evaporation in a vacuum. Column chromatographic purification on silica gel with a hexane-ethyl acetate gradient yields 344 mg of (4-fluoro-butyl)-(5-{4-[6-phenyl-2-(tetrahydropyran-2-yloxy)-8,9-dihydro-7H-benzocyclohepten-5-yl]-phenoxy}-pentyl)-sulfide as a foam.

b) 5-{4-[5-(4-Fluoro-butylthio)-pentyloxy]-phenyl}-6-phenyl-8,9-dihydro-7H-benzocyclohepten-2-ol 336 mg of (4-fluoro-butyl)-(5-{4-[6-phenyl-2-(tetrahydropyran-2-yloxy)-8,9-dihydro-7H-benzocyclohepten-5-yl]-phenoxy]-pentyl)-sulfide is dissolved in 9 ml of methanol, 10 ml of tetrahydrofuran and 0.92 ml of water, mixed with 368 mg of oxalic added in drops and stirred at 50° C. After 2 hours, the further addition of 184 mg of oxalic acid is carried out. After 24 hours, the reaction mixture is cooled to room temperature, mixed with 25 ml of water and stirred for 30 minutes. The deposited precipitation is suctioned off and dried. 275 mg of 5-{4-[5-(4-fluoro-butylthio)-pentyloxy]-phenyl}-6-phenyl-8,9-dihydro-7H-benzocyclohepten-2-ol with a melting point of 163° C. is obtained.

Example 41

5-{4-[5-(4-Fluoro-butanesulfinyl)-pentyloxy]-phenyl}-6-phenyl-8,9-dihydro-7H-benzocyclohepten-2-ol 181 mg of 5-{4-[5-(4-fluoro-butylthio)-pentyloxy]-phenyl}-6-phenyl-8,9-dihydro-7H-benzocyclohepten-2-ol (Example: 40b) is dissolved in 6 ml of methanol and 0.5 ml of water, mixed with 81 mg of sodium periodate and stirred for 2 hours at 50° C. For working-up, the reaction mixture is mixed with dilute sodium chloride solution, extracted three times with methylene chloride, washed with water, dried on magnesium sulfate and concentrated by evaporation in a vacuum. The residue is absorptively precipitated with 10 ml of ether, the solid is suctioned off and dried. 173 mg of 5-{4-[5-(4-fluoro-butanesulfinyl)-pentyloxy]-phenyl}-6-phenyl-8,9-dihydro-7H-benzocyclohepten-2-ol with a melting point of 233° C. is obtained.

Example 42

6-Phenyl-5-{4-[5-(4,4,4-trifluoro-butylthio)-pentyloxy]-phenyl}-8,9-dihydro-7H-benzocyclohepten-2-ol a) (5-{4-[6-Phenyl-2-(tetrahydropyran-2-yloxy)-8,9-dihydro-7H-benzocyclohepten-5-yl]-phenoxy}-pentyl)-(4,4,4-trifluoro-butyl)-sulfide 500 mg of S-(5-{4-[6-phenyl-2-(tetrahydropyran-2-yloxy)-8,9-dihydro-7H-benzocyclohepten-5-yl]-phenoxy}-pentyl)-thioacetate (Example: 12b) is dissolved in 5 ml of tetrahydrofuran and 7.4 ml of methanol and mixed at room temperature drop by drop with 0.2 ml of a 30% methanolic sodium methylate solution. After the addition is completed, it is stirred for 30 more minutes at room temperature before 325 mg of 4,4,4-trifluoro-1-iodobutane is added at the same temperature. After 90 minutes, the reaction mixture is mixed with semisaturated sodium chloride solution, extracted three times with ethyl acetate, washed neutral, dried on magnesium sulfate and concentrated by evaporation in a vacuum. Column chromatographic purification on silica gel with a hexane-ethyl acetate gradient yields 314 mg of (5-{4-(6-phenyl-2-(tetrahydropyran-2-yloxy)-8,9-dihydro-7H-benzocyclohepten-5-yl}-phenoxy}-pentyl)-(4,4,4-trifluoro-butyl)-sulfide as a foam.

b) 6-Phenyl-5-{4-[5-(4,4,4-trifluoro-butylthio)-pentyloxy]-phenyl}-8,9-dihydro-7H-benzocyclohepten-2-ol 310 mg of (5-{4-[6-phenyl-2-(tetrahydropyran-2-yloxy)-8,9-dihydro-7H-benzocyclohepten-5-yl]-phenoxy}-pentyl)-(4,4,4-trifluoro-butyl)-sulfide is dissolved in 8 ml of methanol, 7 ml of tetrahydrofuran and 0.8 ml of water, mixed with 319 mg of oxalic acid and stirred for 3 hours at 50° C. Then, the reaction mixture is cooled to room temperature, mixed with 25 ml of water and stirred for 30 minutes. The deposited precipitate is suctioned off and dried. 243 mg of 6-phenyl-5-{4-[5-(4,4,4-trifluoro-butylthio)-pentyloxy]-phenyl}-8,9-dihydro-7H-benzocyclohepten-2-ol with a melting point of 168° C. is obtained.

Example 43

6-Phenyl-5-{4-[5-(4,4,4-trifluoro-butanesulfinyl)-pentyloxy]-phenyl}-8,9-dihydro-7H-benzocyclohepten-2-ol 109 mg of 6-phenyl-5-{4-[5-(4,4,4-trifluoro-butylthio)-pentyloxy)-phenyl}-8,9-dihydro-7H-benzocyclohepten-2-ol is dissolved at 0° C. in 4 ml of tetrahydrofuran, mixed with 44 mg of m-chloro-perbenzoic acid and stirred at 0° C. After 15 minutes, 15 mg of m-chloro-perbenzoic acid is again added, and the reaction mixture is stirred for another 15 minutes at 0° C. For working-up, the reaction mixture is added to 10% sodium thiosulfate solution, extracted three times with methylene chloride, washed with water, dried on magnesium sulfate and concentrated by evaporation in a vacuum. Column chromatographic purification on silica gel with a methylene chloride-methanol gradient results in 82 mg of 6-phenyl-5-{4-[5-(4,4,4-trifluoro-butanesulfinyl)-pentyloxy]-phenyl}-8,9-dihydro-7H-benzocyclohepten-2-ol with a melting point of 145° C.

Example 44

5-(4-{5-[Methyl-(4,4,5,5,5-pentafluoropentyl)-amino]-pentyloxy}-phenyl)-6-phenyl-8,9-dihydro-7H-benzocyclohepten-2-ol a) methyl-(5-{4-[6-phenyl-2-(tetrahydropyran-2-yloxy)-8,9-dihydro-7H-benzocyclohepten-5-yl]-phenoxy}-pentyl)-amine 914 mg of 2-{5-[4-(5-iodopentyloxy)-phenyl]-6-phenyl-8,9-dihydro-7H-benzocyclohepten-2-yloxy}tetrahydropyran (Example: 12a) is dissovled in a pressure pipe in 5 ml of tetrahydrofuran and about 800 mg of methylamine is condensed at −15° C. Then, the closed pressure pipe is allowed to stand overnight at room temperature. For working-up, the vessel is cooled to −15° C., excess methylamine is evaporated in a nitrogen stream at room temperature, the preparation is added to dilute sodium chloride solution, extracted three times with methylene chloride, dried on magnesium sulfate and concentrated by evaporation in a vacuum. 809 mg of methyl-(5-{4-[6-phenyl-2-(tetrahydropyran-2-yloxy)-8,9-dihydro-7H-benzocyclohepten-5-yl]-phenoxy}-pentyl)-amine is obtained as a crude product, which is used without further purification in the next stage.

b) Methyl-(4,4,5,5,5-pentafluoropentyl)-(5-{4-[6-phenyl-2-(tetrahydropyran-2-yloxy)-8,9-dihydro-7H-benzocyclohepten-5-yl]-phenoxy}-pentyl)-amine 809 mg of methyl-(5-{4-[6-phenyl-2-(tetrahydropyran-2-yloxy)-8,9-dihydro-7H-benzocyclohepten-5-yl]-phenoxy}-pentyl)amine is dissolved in 15 ml of N-methyl-pyrrolidone, mixed in portions with a total of 698 mg of 4,4,5,5,5-pentafluoro-pentyltosylate and stirred for 3 hours at 80° C. After the preparation is cooled to room temperature, the reaction mixture is added to dilute sodium chloride solution, extracted three times with diethyl ether, dried on magnesium sulfate and concentrated by evaporation in a vacuum. Column chromatographic purification on silica gel with a methylene chloride-methanol gradient results in 1.8 g of methyl- (4,4,5,5,5-pentafluoropentyl)-(5-{4-[6-phenyl-2-(tetrahydropyran-2-yloxy)-8,9-dihydro-7H-benzocyclohepten-5-yl]-phenoxy}-pentyl)-amine, which is contaminated with N-methyl-pyrrolidone.

c) 5-(4-{5-[Methyl-(4,4,5,5,5-pentafluoropentyl)-amino]-pentyloxy}-phenyl)-6-phenyl-8,9-dihydro-7H-benzocyclohepten-2-ol 1.8 g of methyl-(4,4,5,5,5-pentafluoropentyl)-(5-{4-[6-phenyl-2-(tetrahydropyran-2-yloxy)-8,9-dihydro-7H-benzocyclohepten-5-yl]-phenoxy}-pentyl)-amine, which is contaminated with N-methyl-pyrrolidone, is dissolved in 25 ml of methanol and 2.5 ml of water, mixed with 1.85 g of oxalic acid and stirred for 90 minutes at 50° C. After the reaction mixture is cooled, it is added to dilute sodium bicarbonate solution, extracted three times with diethyl ether, washed with water, dried on magnesium sulfate and concentrated by evaporation in a vacuum. The residue is put on a column on silica gel with a methylene chloride-methanol gradient. 214 mg of 5-(4-{5-[methyl-(4,4,5,5,5-pentafluoropentyl)-amino]-pentyloxy}-phenyl)-6-phenyl-8,9-dihydro-7H-benzocyclohepten-2-ol is obtained.

Production of the Starting Material 4,4,5,5,5-Pentafluoro-pentyltosylate 6.4 g of p-toluenesulfonyl chloride is introduced into 10 ml of pyridine, mixed drop by drop with 5.44 g of 4,4,5,5,5-pentafluoro-pentan-1-ol at 0° C. and after the addition is completed, it is stirred for 2 hours at room temperature. For working-up, the preparation is taken up in ice-cold 2N hydrochloric acid, extracted three times with diethyl ether, washed with saturated sodium chloride solution, dried on magnesium sulfate and concentrated by evaporation in a vacuum. Column chromatographic purification on silica gel with a hexane-ethyl acetate gradient yields 8.7 g of 4,4,5,5,5-pentafluoro-pentyltosylate as a clear liquid.

Example 45

5-[4-(5-Benzylthio-pentyloxy)-phenyl]-6-phenyl-8,9-dihydro-7H-benzocyclohepten-2-ol a) Benzyl-(5-{4-[6-phenyl-2-(tetrahydropyran-2-yloxy)-8,9-dihydro-7H-benzocyclohepten-5-yl]-phenoxy}-pentyl)-sulfide 1.5 g of S-(5-{4-[6-phenyl-2-(tetrahydropyran-2-yloxy)-8,9-dihydro-7H-benzocyclohepten-5-yl]-phenoxy{-pentyl)-thioacetate (Example: 12b) is dissolved in 10 ml of tetrahydrofuran and 22 ml of methanol and mixed drop by drop at room temperature with 0.6 ml of a 30% methanolic sodium methylate solution. After the addition is completed, it is stirred for 30 more minutes at room temperature, before 0.5 ml of benzylbromide is added in drops at the same temperature. After 2 hours, the reaction mixture is mixed with dilute sodium chloride solution, extracted three times with ethyl acetate, washed neutral, dried on magnesium sulfate and concentrated by evaporation in a vacuum. Column chromatographic purification on silica gel with a hexane-ethyl acetate gradient yields 1.12 g of benzyl-(5-{4-[6-phenyl-2-(tetrahydropyran-2-yloxy)-8,9-dihydro-7H-benzocyclohepten-5-yl]-phenoxy}-pentyl)-sulfide as a foam.

b) 5-[4-(5-Benzylthio-pentyloxy)-phenyl]-6-phenyl-8,9-dihydro-7H-benzocyclohepten-2-ol 1.12 g of benzyl-(5-{4-(6-phenyl-2-(tetrahydropyran-2-yloxy)-8,9-dihydro-7H-benzocyclohepten-5-yl]-phenoxy}{-pentyl)-sulfide is dissolved in 27 ml of methanol, 3 ml of tetrahydrofuran and 2.7 ml of water, mixed with 1.16 g of oxalic acid and stirred for 3 hours at 50° C. Then, the reaction mixture is cooled to room temperature, mixed with 5 ml of water and stirred for 5 minutes. The deposited precipitate is suctioned off and dried. 855 mg of 5-[4-(5-benzylthio-pentyloxy)-phenyl]-6-phenyl-8,9-dihydro-7H-benzocyclohepten-2-ol with a melting point of: 178–186° C. is obtained.

Example 46

5-[4-(5-Benzylsulfinyl-pentyloxy)-phenyl]-6-phenyl-8,9-dihydro-7H-benzocyclohepten-2-ol 555 mg of 5-[4-(5-benzylthio-pentyloxy)-phenyl]-6-phenyl-8,9-dihydro-7H-benzocyclohepten-2-ol (Example: 45) is dissolved in 17 ml of methanol, 15 ml of ethyl acetate and 1 ml of water, mixed with 241 mg of sodium periodate and stirred first at room temperature and later for 3 hours at 50° C. For working-up, the reaction mixture is mixed with dilute sodium chloride solution, extracted three times with methylene chloride, washed with water, dried on magnesium sulfate and concentrated by evaporation in a vacuum. By column chromatographic purification on silica gel with a hexane-ethyl acetate gradient, 469 mg of 5-[4-(5-benzylsulfinyl-pentyloxy)-phenyl]-6-phenyl-8,9-dihydro-7H-benzocyclohepten-2-ol with a melting point of: 196° C. is obtained.

Example 47

5-{4-[5-(4-Methyl-benzylthio)-pentyloxy]-phenyl}-6-phenyl-8,9-dihydro-7H-benzocyclohepten-2-ol a) (4-Methyl-benzyl)-(5-{4-[6-phenyl-2-(tetrahydropyran-2-yloxy)-8,9-dihydro-7H-benzocyclohepten-5-yl]-phenoxy}-pentyl)-sulfide 1.5 g of S-(5-{4-[6-phenyl-2-(tetrahydropyran-2-yloxy)-8,9-dihydro-7H-benzocyclohepten-5-yl]-phenoxy}-pentyl)-thioacetate (Example: 12b) is dissolved in 5 ml of tetrahydrofuran and 20 ml of methanol and mixed drop by drop at room temperature with 0.6 ml of a 30% methanolic sodium methylate solution. After the addition is completed, it is stirred for 30 more minutes at room temperature before 757 mg of 4-methyl-benzylbromide in 5 ml of tetrahydrofuran is added in drops at the same temperature. After 2 hours, the reaction mixture is mixed with dilute sodium chloride solution, extracted three times with ethyl acetate, washed neutral, dried on magnesium sulfate and concentrated by evaporation in a vacuum. Column chromatographic purification on silica gel with a hexane-ethyl acetate gradient yields 1.24 g of (4-methyl-benzyl)-(5-{4-[6-phenyl-2-(tetrahydropyran-2-yloxy)-8,9-dihydro-7H-benzocyclohepten-5-yl]-phenoxy}-pentyl)-sulfide as a foam.

b) 5-{4-[5-(4-Methyl-benzylthio)-pentyloxy]-phenyl}=6-phenyl-8,9-dihydro-7H-benzocyclohepten-2-ol 250 mg of (4-methyl-benzyl)-(5-{4-[6-phenyl-2-(tetrahydropyran-2-yloxy)-8,9-dihydro-7H-benzocyclohepten-5-yl]-phenoxy}-pentyl)-sulfide is dissolved in 6 ml of methanol, 1 ml of tetrahydrofuran and 0.6 ml of water, mixed with 258 mg of oxalic acid and stirred for 3 hours at 50° C. Then, the reaction mixture is cooled to room temperature, mixed with 5 ml of water and stirred for

Example 48

5-{4-[5-(4-Methyl-benzylsulfinyl)-pentyloxy]-phenyl}-6-phenyl-8,9-dihydro-7H-benzocyclohepten-2-ol 5 minutes. The deposited precipitate is suctioned off and dried. 196 mg of 5-{4-[5-(4-methyl-benzylthio)-pentyloxy]-phenyl}-6-phenyl-8,9-dihydro-7H-benzocyclohepten-2-ol with a melting point of 165–169° C. is obtained.

600 mg of 5-{4-[5-(4-methyl-benzylthio)-pentyloxy]-phenyl}-6-phenyl-8,9-dihydro-7H-benzocyclohepten-2-ol (Example: 47b) is dissolved in 18 ml of methanol, 15 ml of ethyl acetate and 1 ml of water, mixed with 252 mg of sodium periodate and stirred first at room temperature and later for 3 hours at 50° C. For working-up, the reaction mixture is mixed with dilute sodium chloride solution, extracted three times with methylene chloride, washed with water, dried on magnesium sulfate and concentrated by evaporation in a vacuum. By column chromatographic purification on silica gel with a hexane-ethyl acetate gradient, 248 mg of 5-{4-[5-(4-methyl-benzylsulfinyl)-pentyloxy]-phenyl}-6-phenyl-8,9-dihydro-7H-benzocyclohepten-2-ol is obtained.

Example 49

6-Phenyl-5-{4-[5-(4-trifluoromethyl-benzylthio)-pentyloxy]-phenyl}-8,9-dihydro-7H-benzocyclohepten-2-ol a) (5-{4-[6-Phenyl-2-(tetrahydropyran-2-yloxy)-8,9-dihydro-7H-benzocyclohepten-5-yl]-phenoxy}-pentyl)-(4-trifluoromethyl-benzyl)-sulfide 1.5 g of S-(5-{4-[6-phenyl-2-(tetrahydropyran-2-yloxy)-8,9-dihydro-7H-benzocyclohepten-5-yl]-phenoxy}-pentyl)-thioacetate (Example: 12b) is dissolved in 10 ml of tetrahydrofuran and 20 ml of methanol and mixed drop by drop at room temperature with 0.6 ml of a 30% methanolic sodium methylate solution. After the addition is completed, it is stirred for 30 more minutes at room temperature before 977 mg of 4-(trifluoromethyl)benzylbromide in 5 ml of tetrahydrofuran is added in drops at the same temperature. After 2 hours, the reaction mixture is mixed with dilute sodium chloride solution, extracted three times with ethyl acetate, washed neutral, dried on magnesium sulfate and concentrated by evaporation in a vacuum.

Column chromatographic purification on silica gel with a hexane-ethyl acetate gradient yields 1.15 g of (5-{4-[6-phenyl-2-(tetrahydropyran-2-yloxy)-8,9-dihydro-7H-benzocyclohepten-5-yl]-phenoxy}-pentyl)-(4-trifluoromethyl-benzyl)-sulfide as a foam.

b) 6-Phenyl-5-{4-[5-(4-trifluoromethyl-benzylthio)-pentyloxy]-phenyl}-8,9-dihydro-7H-benzocyclohepten-2-ol 1.14 g of (5-{4-[6-phenyl-2-(tetrahydropyran-2-yloxy)-8,9-dihydro-7H-benzocyclohepten-5-yl]-phenoxy}-pentyl)-(4-trifluoromethyl-benzyl)-sulfide is dissolved in 27 ml of methanol, 3 ml of tetrahydrofuran and 2.7 ml of water, mixed with 1.16 g of oxalic acid and stirred for 3 hours at 50° C. Then, the reaction mixture is cooled to room temperature, mixed with 5 ml of water, and stirred for 5 minutes. The deposited precipitate is suctioned off and dried. 933 mg of 6-phenyl-5-{4-[5-(4-trifluoromethyl-benzylthio)-pentyloxy]-phenyl}-8,9-dihydro-7H-benzocyclohepten-2-ol with a melting point of 147° C. is obtained.

Example 50

6-Phenyl-5-{4-[5-(4-trifluoromethyl-benzylsulfinyl)-pentyloxy]-phenyl}-8,9-dihydro-7H-benzocyclohepten-2-ol 600 mg of 6-phenyl-5-{4-[5-(4-trifluoromethyl-benzylthio)-pentyloxy]-phenyl}-8,9-dihydro-7H-benzocyclohepten-2-yl (Example: 49b) is dissolved in 16 ml of methanol, 15 ml of ethyl acetate and 1 ml of water, mixed with 230 mg of sodium periodate and stirred first at room temperature and later for 3 hours at 50° C. For working-up, the reaction mixture is mixed with dilute sodium chloride solution, extracted three times with methylene chloride, washed with water, dried ion magnesium sulfate and concentrated by evaporation in a vacuum. By column chromatographic purification on silica gel with a hexane-ethyl acetate gradient, 494 mg of 6-phenyl-5-{4-[5-(4-trifluoromethyl-benzylsulfinyl)-pentyloxy]-phenyl}-8,9-dihydro-7H-benzocyclohepten-2-ol is obtained.

Example 51

6-Phenyl-5-[4-(5-phenylthio-pentyloxy)-phenyl]-8,9-dihydro-7H-benzocyclohepten-2-ol a) Phenyl-(5-{4-[6-phenyl-2-(tetrahydropyran-2-yloxy)-8,9-dihydro-7H-benzocyclohepten-5-yl]-phenoxy}-pentyl)-sulfide 1.0 g of 2-{5-[4-(5-iodopentyloxy)-phenyl]-6-phenyl-8,9-dihydro-7H-benzocyclohepten-2-yloxy}-tetrahydropyran (Example: 12a) is dissolved in 5 ml of tetrahydrofuran and mixed at room temperature with 0.34 ml of 30% aqueous potassium hydroxide solution and 0.17 ml of thiophenol. Then, it is stirred for 4 hours at 90° C. For working-up, the reaction mixture is allowed to reach room temperature, diluted with diethyl ether, washed three times with water, dried on magnesium sulfate and concentrated by evaporation in a vacuum. Column chromatographic purification on silica gel with a hexane-ethyl acetate gradient yields 816 mg of phenyl-(5-{4-[6-phenyl-2-(tetrahydropyran-2-yloxy)-8,9-dihydro-7H-benzocyclohepten-5-yl]-phenoxy}-pentyl-sulfide as a foam.

b) 6-Phenyl-5-[4-(5-phenylthio-pentyloxy)-phenyl]-8,9-dihydro-7H-benzocyclohepten-2-ol 816 mg of phenyl-(5-{4-[6-phenyl-2-(tetrahydropyran-2-yloxy-8,9-dihydro-7H-benzocyclohepten-5-yl}-phenoxy}-pentyl)-sulfide is dissolved in 20 ml of methanol, 5 ml of tetrahydrofuran and 2 ml of water, mixed with 890 mg of oxalic acid and stirred for 90 minutes at 50° C. Then, the reaction mixture is cooled to room temperature, mixed with 25 ml of water and stirred for 30 minutes. The deposited precipitate is suctioned off and dried. 670 mg of 6-phenyl-5-[4-(5-phenylthio-pentyloxy)-phenyl]-8,9-dihydro-7H-benzocyclohepten-2-yl with a melting point of 192° C. is obtained.

Examples 52 and 53

6-Phenyl-5-[4-(5-phenylsulfinyl-pentyloxy)-phenyl]-8,9-dihydro-7H-benzocyclohepten-2-ol and 6-phenyl-5-[4-(5-phenylsulfonyl-pentyloxy)-phenyl]-8,9-dihydro-7H-benzocyclohepten-2-ol 109 mg of 6-phenyl-5-[4-(5-phenylthio-pentyloxy)-phenyl]-8,9-dihydro-7H-benzocyclohepten-2-ol (Example:

51b) is introduced at 0° C. into 8 ml of methylene chloride and mixed with 57 mg of m-chloroperbenzoic acid. After 1.5 hours of stirring under cold conditions, the reaction is completed by adding sodium thiosulfate solution. Then, the preparation is mixed with saturated sodium bicarbonate solution, extracted three times with methylene chloride, washed neutral, dried on magnesium sulfate and evaporated to the dry state in a vacuum. Preparative thin-layer chromatography with a hexane-ethyl acetate mixture yields 22 mg of 6-phenyl-5-[4-(5-phenylsulfonyl-pentyloxy)-phenyl]-8,9-dihydro-7H-benzocyclohepten-2-ol with a melting point of 162° C. and 75 mg of 6-phenyl-5-[4-(5-phenylsulfinyl-pentyloxy)-phenyl]-8,9-dihydro-7H-benzocyclohepten-2-ol.

Example 54

5-{4-[5-(4-tert-Butyl-phenylthio)-pentyloxy]-phenyl}-6-phenyl-8,9-dihydro-7H-benzocyclohepten-2-ol a) (4-tert-Butyl-phenyl)-5-{4-[6-phenyl-2-(tetrahydropyran-2-yloxy)-8,9-dihydro-7H-benzocyclohepten-5-yl]-phenoxy}-pentyl)-sulfide 1.5 g of 2-{5-[4-(5-iodopentyloxy)-phenyl]-6-phenyl-8,9-dihydro-7H-benzocyclohepten-2-yloxy}-tetrahydropyran (example: 12a) is dissolved in 7.5 ml of tetrahydrofuran and mixed at room temperature with 0.51 ml of of 30% aqueous potassium hydroxide solution and 409 mg of 4-tert-butylthiophenol. Then, it is stirred for 1 hour at 90° C. For working-up, the reaction mixture is allowed to reach room temperature, diluted with diethyl ether, washed twice with water, dried on magnesium sulfate and concentrated by evaporation in a vacuum. Column chromatographic purification on silica gel with a hexane-diehtyl ether gradient yields 1.35 g of (4-tert-butyl-phenyl)-(5-{4-[6-phenyl-2-(tetrahydropyran-2-yloxy)-8,9-dihydro-7H-benzocyclohepten-5-yl]-phenoxy}-pentyl)-sulfide as a foam.

b) 5-{4-[5-(4-tert-Butyl-phenylthio)-pentyloxy]-phenyl}-6-phenyl-8,9-dihydro-7H-benzocyclohepten-2-ol 1.34 g of (4-tert-butyl-phenyl)-(5-{4-[6-phenyl-2-(tetrahydropyran-2-yloxy)-8,9-dihydro-7H-benzocyclohepten-5-yl]-phenoxy}-pentyl)-sulfide is dissovled in 30 ml of methanol, 3 ml of tetrahydrofuran and 3 ml of water, mixed with 1.33 g of oxalic acid and stirred for 5 hours at 50° C. Then, the reaction mixture is cooled to room temperature, mixed with 10 ml of water and stirred for 15 minutes. The deposited precipitate is suctioned off and dried. Preparative column chromatography on silica gel with a hexane-ethyl acetate gradient yields 946 mg of 5-{4-[5-(4-tert-butyl-phenylthio)-pentyloxy]-phenyl}-6-phenyl-8,9-dihydro-7H-benzocyclohepten-2-ol with a melting point of 139° C.

Examples 55 and 56

5-{4-[5-(4-tert-Butyl-phenylsulfinyl)-pentyloxy]-phenyl}-6-phenyl-8,9-dihydro-7H-benzocyclohepten-2-ol and 5-{4-[5-(4-tert-butyl-phenylsulfonyl)-pentyloxy]-phenyl}-6-phenyl-8,9-dihydro-7H-benzocyclohepten-2-ol 450 mg of 5-{4-[5-(4-tert-butyl-phenylthio)-pentyloxy]-phenyl}-6-phenyl-8,9-dihydro-7H-benzocyclohepten-2-ol (Example: 54b) is introduced at 0° C. in 30 ml of methylene chloride and mixed with 206 mg of m-chloroperbenzoic acid. After 1 hour of stirring under cold conditions, the preparation is mixed with saturated sodium bicarbonate solution, extracted three times with methylene chloride, washed neutral, dried on magnesium sulfate and evaporated to the dry state in a vacuum. Preparative column chromatography on silica gel with a hexane-ethyl acetate gradient yields 32 mg of 5-{4-[5-(4-tert-butyl-phenylsulfonyl)-pentyloxy]-phenyl}-6-phenyl-8,9-dihydro-7H-benzocyclohepten-2-ol and 412 mg of 5-{4-[5-(4-tert-butyl-phenylsulfinyl)-pentyloxy]-phenyl}-6-phenyl-8,9-dihydro-7H-benzocyclohepten-2-ol.

Example 57

6-Phenyl-5-{4-[5-(4-trifluoromethyl-phenylthio)-pentyloxy]-phenyl}-8,9-dihydro-7H-benzocyclohepten-2-ol a) (5-{4-[6-Phenyl-2-(tetrahydropyran-2-yloxy)-8,9-dihydro-7H-benzocyclohepten-5-yl]-phenoxy}-pentyl)-(4-trifluoromethyl-phenyl)-sulfide 1.5 g of 2-{5-[4-(5-iodopentyloxy)-phenyl]-6-phenyl-8,9-dihydro-7H-benzocyclohepten-2-yloxy}-tetrahydropyran (example: 12a) is dissolved in 7.5 ml of tetrahydrofuran and mixed at room temperature with 0.51 ml of 30% aqueous potassium hydroxide solution and 438 mg of 4-(trifluoromethyl)-thiophenol. Then, it is stirred for 1 hour at 90° C. For working-up, the reaction mixture is allowed to reach room temperature, diluted with diethyl ether, washed twice with water, dried on magnesium sulfate and concentrated by evaporation in a vacuum. Column chromatographic purification on silica gel with a hexane-diehtyl ether gradient yields 1.28 g of (5-{4-[6-phenyl-2-(tetrahydropyran-2-yloxy)-8,9-dihydro-7H-benzocyclohepten-5-yl]-phenoxy}-pentyl)-(4-trifluoromethyl-phenyl)-sulfide.

b) 6-Phenyl-5-{4-[5-(4-trifluoromethyl-phenylthio)-pentyloxy]-phenyl}-8,9-dihydro-7H-benzocyclohepten-2-ol 1.28 g of (5-{4-[6-phenyl-2-(tetrahydropyran-2-yloxy)-8,9-dihydro-7H-benzocyclohepten-5-yl]-phenoxy}-pentyl)-(4-trifluoromethyl-phenyl)-sulfide is dissovled in 29 ml of methanol, 3 ml of tetrahydrofuran and 3 ml of water, mixed with 1.25 g of oxalic acid and stirred for 5 hours at 50° C. Then, the reaction mixture is cooled to room temperature, mixed with 10 ml of water and stirred for 15 minutes. The deposited precipitate is suctioned off and dried. Recrystallization from ethyl acetate yields 890 mg of 6-(phenyl-5-{4-[5-(4-trifluoromethyl-phenylthio)-pentyloxy]-phenyl}-8,9-dihydro-7H-benzocyclohepten-2-ol with a melting point of: 189° C.

Examples 58 and 59

6-Phenyl-5-{4-[5-(4-trifluoromethyl-phenylsulfinyl)-pentyloxy]-phenyl}-8,9-dihydro-7H-benzocyclohepten-2-ol and 6-phenyl-5-{4-[5-(4-trifluoromethyl-phenylsulfonyl)-pentyloxy]-phenyl}-8,9-dihydro-7H-benzocyclohepten-2-ol 425 mg of 6-phenyl-5-{4-[5-(4-trifluoromethyl-phenylthio)-pentyloxy[-phenyl}-8,9-dihydro-7H- benzocyclohepten-2-ol (Example: 57b) is introduced at 0° C. into 28 ml of methylene chloride and mixed with 190 mg of m-chloroperbenzoic acid. After 1 hour of stirring under cold conditions, the preparation is mixed with saturated sodium bicarbonate solution, extracted three times with methylene chloride, washed neutral, dried on magnesium sulfate and evaporated to the dry state in a vacuum. Preparative column chromatography on silica gel with a hexane-ethyl acetate gradient yields 71 mg of 6-phenyl-5-{4-[5-(4-trifluoromethyl-phenylsulfonyl)-pentyloxy]-phenyl}-8,9-dihydro-7H-benzocyclohepten-2-ol with a melting point of: 187° C. and 325 mg of 6-phenyl-5-{4-[5-(4-trifluoromethyl-phenylsulfinyl)-pentyloxy]-phenyl}-8,9-dihydro-7H-benzocyclohepten-2-ol.

What is claimed is:

1. A benzocycloheptene of formula I

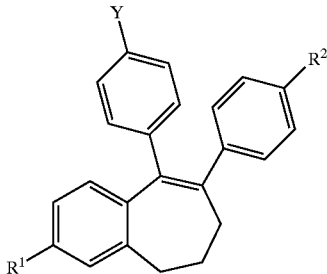

in which
- $R^1$ and $R^2$, independently of one another, is H, a hydroxy group, an optionally substituted $C_1$–$C_{10}$ alkoxy group, an optionally substituted $C_1$–$C_{10}$ alkanoyloxy group or an optionally substituted $C_7$–$C_{15}$ aroyloxy group;
- Y is a side chain —A—B—Z;
- A is a direct bond or an oxygen atom;
- B is a straight-chain or branched-chain, optionally substituted alkylene, alkenylene or alkinylene group with up to 10 carbon atoms;
- Z is a group —D—SO$_x$—E—G, an amino group —NR$^7$R$^8$ or a substituent G;
- D is a direct bond or a group —NR$^3$(R$^4$—);
- $R^3$ is a straight-chain or branched-chain alkyl, alkenyl or alkinyl group with up to 10 carbon atoms;
- $R^4$ is a straight-chain or branched-chain, optionally substituted alkylene, alkenylene or alkinylene group with up to 10 carbon atoms;
- x is 0, 1 or 2;
- E is a straight-chain or branched-chain, optionally substituted alkylene, alkenylene or alkinylene group with up to 10 carbon atoms;
- G is a partially or completely fluorinated straight-chain or branched-chain alkyl group with up to 5 carbon atoms, an optionally substituted aryl radical, a carbamoyl radical —C(O)—NR$^5$R$^6$, a halogen atom or a hydrogen atom; $R^5$, $R^6$, $R^7$ $R^8$, independently of one another, are each H, a straight chain or branched-chain, optionally partially fluorinated alkyl, alkenyl or alkinyl radical with up to 14 carbon atoms, which is optionally interrupted by one to three heteroatoms —O— and —S— or groupings —NR$^9$—, an aryl radical that is optionally substituted in one or two places, a $C_3$–$C_{10}$ cycloalkyl radical that is optionally substituted in one or two places, a $C_4$–$C_{15}$ cycloalkylalkyl radical that is optionally substituted in one or two places, a $C_7$–$C_{20}$ aralkyl radical that is optionally substituted in one or two places, an optionally substituted aminoalkyl radical, a biphenylene radical or a radical of formula —C(O)R$^{10}$;
- $R^9$ is H or $C_{1-3}$ alkyl; and
- $R^{10}$ is H, a straight chain or branched-chain, optionally partially fluorinated alkyl, alkenyl or alkinyl radical with up to 14 carbon atoms, which is optionally interrupted by one to three heteroatoms —O— and —S— or groupings —NR$^9$, an aryl radical that is optionally substituted in one or two places, a $C_3$–$C_{10}$ cycloalkyl radical that is optionally substituted in one or two places, a $C_4$–$C_{15}$ cycloalkylalkyl radical that is optionally substituted in one or two places, a $C_7$–$C_{20}$ aralkyl radical that is optionally substituted in one or two places, an optionally substituted aminoalkyl radical, or a biphenylene radical; or a physiologically compatible salt thereof;

wherein
in —A—B—Z, if A is an oxygen atom and Z is G, G cannot be a hydrogen atom or a halogen atom, or if A is an oxygen atom and Z is an amino group —NR$^7$R$^8$, in which R$^7$ and R$^8$ in each case a methyl group, B has at least 3 carbon atoms, or if B is —CH$_2$H$_4$— and Z is —NR$^7$R, then R$^7$ and R$^8$ are not the same.

2. A compound according to claim 1, in which $R^1$ and/or $R^2$ is a hydrogen atom.

3. A compound according to claim 1, in which A is an oxygen atom.

4. A compound according to claim 1, in which B is a straight-chain alkylene chain with 1 to 6 carbon atoms.

5. A compound according to claim 1, in which side chain Y is selected from the group of the following side chains —O—(CH$_2$)$_5$S(CH$_2$)$_3$C$_2$F$_5$
—O—(CH$_2$)$_5$SO(CH$_2$)$_3$C$_2$F$_5$
—O—(CH$_2$)$_5$SO$_2$(CH$_2$)$_3$C$_2$F$_5$
—O—(CH$_2$)$_2$—N(CH3)—(CH$_2$)$_3$—S—(CH$_2$)$_3$C$_2$F$_5$
—O—(CH$_2$)$_2$—N(CH3)—(CH$_2$)$_3$—SO—(CH$_2$)$_3$C$_2$F$_5$
—O—(CH$_2$)$_5$S(CH$_2$)—C(O)N(CH$_3$)—(CH$_2$)$_3$CH$_3$
—O—(CH$_2$)$_5$SO(CH$_2$)—C(O)N(CH$_3$)—(CH$_2$)$_3$CH$_3$
—O—(CH$_2$)$_2$—NH(CH$_2$)OH
—O—(CH$_2$)$_2$—N(CH3)—(CH$_2$)$_2$—SO(CH$_2$)—C(O)N(CH$_3$)—(CH$_2$)$_3$CH$_3$
—O—(CH$_2$)$_2$—N(CH3)—(CH$_2$)$_2$—SO$_2$(CH$_2$)—C(O)N(CH$_3$)—(CH$_2$)$_3$CH$_3$
—O—(CH$_2$)$_6$S(CH$_2$)—C(O)N(CH$_3$)—(CH$_2$)$_3$CH$_3$
—O—(CH$_2$)$_6$SO(CH$_2$)—C(O)N(CH$_3$)—(CH$_2$)$_3$CH$_3$
—O—CH$_3$
—O—(CH$_2$)$_5$—F
—O—(CH$_2$)$_4$—F
—O—(CH$_2$)$_3$—F
—O—(CH$_2$)$_2$—F
—O—(CH$_2$)$_5$—Cl
—O—(CH$_2$)$_4$—Cl
—O—(CH$_2$)$_3$—Cl
—O—(CH$_2$)$_2$—Cl
—O—(CH$_2$)$_6$S(CH$_2$)$_3$C$_2$F$_6$
—O—(CH$_2$)$_6$SO(CH$_2$)$_3$C$_2$F$_6$
—O—(CH$_2$)$_5$S(CH$_2$)$_2$C$_3$F$_7$
—O—(CH$_2$)$_4$S(CH$_2$)$_3$C$_2$F$_5$
—O—(CH$_2$)$_4$SO(CH$_2$)$_3$C$_2$F$_5$ —O—(CH$_2$)$_4$SO$_2$(CH$_2$)$_3$C$_2$F$_5$
—O—(CH$_2$)$_5$S(CH$_2$)$_4$—F
—O—(CH$_2$)$_5$SO(CH$_2$)$_4$—F
—O—(CH$_2$)$_5$S(CH$_2$)$_3$—CF$_3$
—O—(CH$_2$)$_5$SO(CH$_2$)$_3$—CF$_3$
—O—(CH$_2$)$_5$—N(CH$_3$)—(CH$_2$)$_3$—C$_2$F$_5$
—O—(CH$_2$)$_5$S(CH$_2$)-Phenyl
—O—(CH$_2$)$_5$SO(CH$_2$)-2-Phenyl
—O—(CH$_2$)$_5$S(CH$_2$)-p-Tolyl
—O—(CH$_2$)$_5$SO(CH$_2$)-p-Tolyl
—O—(CH$_2$)$_5$S(CH$_2$)-p-CF$_3$-Phenyl
—O—(CH$_2$)$_5$SO(CH$_2$)-p-CF$_3$-Phenyl
—O—(CH$_2$)$_5$S-Phenyl
—O—(CH$_2$)$_5$SO-Phenyl
—O—(CH$_2$)$_5$S-(p-Tolyl)
—O—(CH$_2$)$_5$SO-(p-Tolyl)
—O—(CH$_2$)$_5$S-(p-CF$_3$-Phenyl)
—O—(CH$_2$)$_5$SO-(p-CF$_3$-Phenyl).

6. A compound according to claim 1, in which side chain Y is selected from the group of the following side chains —(CH$_2$)$_5$N(CH$_3$)(CH$_2$)$_3$C$_2$F$_5$
—(CH$_2$)$_5$N(CH$_3$)(CH$_2$)$_6$C$_2$F$_5$
—(CH$_2$)$_5$N(CH$_3$)(CH$_2$)$_7$C$_2$F$_5$
—(CH$_2$)$_5$N(CH$_3$)(CH$_2$)$_8$C$_2$F$_5$
—(CH$_2$)$_6$N(CH$_3$)(CH$_2$)$_6$C$_2$F$_5$
—(CH$_2$)$_6$N(CH$_3$)(CH$_2$)$_7$C$_2$F$_5$
—(CH$_2$)$_6$N(CH$_3$)(CH$_2$)$_8$C$_2$F$_5$
—(CH$_2$)$_5$N(CH$_3$)(CH$_2$)$_2$C$_4$F$_9$
—(CH$_2$)$_5$N(CH$_3$)(CH$_2$)$_3$C$_6$F$_{13}$
—(CH$_2$)$_5$N(CH$_3$)(CH$_2$)$_3$C$_8$F$_{17}$
—(CH$_2$)$_5$N(CH$_3$)(CH$_2$)$_6$C$_4$F$_9$
—(CH$_2$)$_5$N(CH$_3$)(CH$_2$)$_6$C$_6$F$_{13}$
—(CH$_2$)$_5$N(CH$_3$)(CH$_2$)$_6$C$_8$F$_{17}$
—(CH$_2$)$_5$N(CH$_3$)H
—(CH$_2$)$_5$N(CH$_3$)(CH$_2$)$_9$H
—(CH$_2$)$_9$S(CH$_2$)$_3$C$_2$F$_5$
—(CH$_2$)$_9$SO(CH$_2$)$_3$C$_2$F$_5$
—(CH$_2$)$_9$SO$_2$(CH$_2$)$_3$C$_2$F$_5$.

7. A compound according to claim 1, in which side chain Y is selected from the partial formula

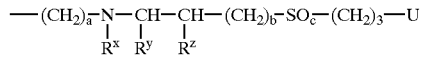

wherein
a is 4, 5 or 6,
b is 0, 1 or 2,
c is 0, 1 or 2,
R$^x$ is a hydrogen atom or a C$_{1-5}$ alkyl group, R$^y$ and R$^z$ are each a hydrogen atom, and
U is ethyl or ethyl that is fluorinated in one to five places, or
the terminal substituent —(CH$_2$)$_3$—U in the side chain is replaced by an optionally substituted aryl, which is bonded directly or via a mono-, di- or trimethylene group to the sulfur atom.

8. A compound according to claim 7, in which Y is the side chain —(CH$_2$)$_5$N(CH$_3$)(CH$_2$)$_3$S(CH$_2$)$_3$C$_2$F$_5$.

9. A compound according to claim 1, wherein said compound is:

(4,4,5,5,5-Pentafluoropentyl)-{5-[4-(6-phenyl-8,9-dihydro-7H-benzocyclohepten-5-yl)-phenoxy]-pentyl}-sulfide,
(4,4,5,5,5-pentafluoropentyl)-{5-[4-(6-phenyl-8,9-dihydro-7H-benzocyclohepten-5-yl)-phenoxy]-pentyl}-sulfoxide,
methyl-[3-(4,4,5,5,5-pentafluoropentylthio)-propyl]-{2-[4-(6-phenyl-8,9-dihydro-7H-benzocyclohepten-5-yl)-phenoxy]-ethyl}-amine,
methyl-[3-(4,4,5,5,5-pentafluoropentylsulfinyl)-propyl]-{2-[4-(6-phenyl-8,9-dihydro-7H-benzocyclohepten-5-yl)-phenoxy]-ethyl}-amine,
S-{5-[4-(6-phenyl-8,9-dihydro-7H-benzocyclohepten-5-yl)-phenoxy]-pentyl}-thioacetate,
N-butyl-N-methyl-2-{5-[4-(6-phenyl-8,9-dihydro-7H-benzocyclohepten-5-yl)-phenoxy]-pentylthio}-acetamide,
N-butyl-N-methyl-2-{5-[4-(6-phenyl-8,9-dihydro-7H-benzocyclohepten-5-yl)-phenoxy]-pentanesulfinyl}-acetamide,
5-{4-[5-(4,4,5,5,5-pentafluoro-pentylthio)-pentyloxy]-phenyl}-6-phenyl-8,9-dihydro-7H-benzocyclohepten-2-ol,
5-{4-[5-(4,4,5,5,5-pentafluoro-pentanesulfinyl)-pentyloxy]-phenyl}-6-phenyl-8,9-dihydro-7H-benzocyclohepten-2-ol,
5-[4-(2-{methyl-[3-(4,4,5,5,5-pentafluoro-pentanesulfinyl)-propyl]-amino}-ethoxy)-phenyl]-6-phenyl-8,9-dihydro-7H-benzocyclohepten-2-ol,
5-[4-(2-{methyl-[3-(4,4,5,5,5-pentafluoro-pentylthio)-propyl]-amino}-ethoxy)-phenyl]-6-phenyl-8,9-dihydro-7H-benzocyclohepten-2-ol,
N-butyl-N-methyl-2-{5-[4-(2-hydroxy-6-phenyl-8,9-dihydro-7H-benzocyclohepten-5-yl)-phenoxy]-pentylthio}-acetamide,
5-{4-[5-(4,4,5,5,5-pentafluoro-pentanesulfonyl)-pentyloxy]-phenyl}-6-phenyl-8,9-dihydro-7H-benzocyclohepten-2-ol,
N-butyl-N-methyl-2-{5-[4-(2-hydroxy-6-phenyl-8,9-dihydro-7H-benzocyclohepten-5-yl)-phenoxy]-pentanesulfinyl}-acetamide,
N-butyl-2-[2-({2-[4-(2-hydroxy-6-phenyl-8,9-dihydro-7H-benzocyclohepten-5-yl)-phenoxy]-ethyl}-methyl-amino)-ethanesulfinyl]-N-methyl-acetamide,
N-butyl-2-[2-({2-[4-(2-hydroxy-6-phenyl-8,9-dihydro-7H-benzocyclohepten-5-yl)-phenoxy]-ethyl}-methyl-amino)-ethanesulfonyl]-N-methyl-acetamide,
6-(4-hydroxy-phenyl)-5-{4-[5-(4,4,5,5,5-pentafluoro-pentanesulfonyl)-pentyloxy]-phenyl}-8,9-dihydro-7H-benzocyclohepten-2-ol,
N-butyl-2-{6-[4-(2-hydroxy-6-phenyl-8,9-dihydro-7H-benzocyclohepten-5-yl)-phenoxy]-hexanesulfinyl}-N-methyl-acetamide,
N-butyl-2-{6-[4-(2-hydroxy-6-phenyl-8,9-dihydro-7H-benzocyclohepten-5-yl)-phenoxy]-hexylthio}-N-methyl-acetamide,
6-(4-hydroxy-phenyl)-5-{4-[5-(4,4,5,5,5-pentafluoropentylthio)-pentyloxy]-phenyl}-8,9-dihydro-7H-benzocyclohepten-2-ol,
6-(4-hydroxy-phenyl)-5-{4-[5-(4,4,5,5,5-pentafluoropentane-sulfinyl)-pentyloxy]-phenyl}-8,9-dihydro-7H-benzocyclohepten-2-ol,
5-{4-[4-(4,4,5,5,5-pentafluoro-pentylthio)-butyloxy]-phenyl}-6-phenyl-8,9-dihydro-7H-benzocyclohepten-2-ol, 5-{4-[4-(4,4,5,5,5-pentafluoro-pentanesulfinyl)-butyloxy]-phenyl}-6-phenyl-8,9-dihydro-7H-benzocyclohepten-2-ol, 5-{4-[6-(4,4,5,5,5-pentafluoro-pentylthio)-hexyloxy]-phenyl}-6-phenyl-8,9-dihydro-7H-benzocyclohepten-2-ol, 5-{4-[6-(4,4,5,5,5-pentafluoro-pentanesulfinyl)-hexyloxy]-phenyl}-6-phenyl-8,9-dihydro-7H-benzocyclohepten-2-ol, 5-{4-[5-(3,3,4,4,5,5,5-heptafluoro-pentylthio)-pentyloxy]-phenyl}-6-phenyl-8,9-dihydro-7H-benzocyclohepten-2-ol, 5-{4-[2-(2-hydroxy-ethylamino)-ethoxy]-phenyl}-6-phenyl-8,9-dihydro-7H-benzocyclohepten-2-ol, 5-{4-[5-(4-fluoro-butylthio)-pentyloxy]-phenyl}-6phenyl-8,9-dihydro-7H-benzocyclohepten-2-ol, 5-{4-[5-(4-fluoro-butanesulfinyl)-pentyloxy]-phenyl}-6-phenyl-8,9-dihydro-7H-benzocyclohepten-2-ol, 6-phenyl-5-{4-[5-(4,4,4-trifluoro-butylthio)-pentyloxy]-phenyl}-8,9-dihydro-7H-benzocyclohepten-2-ol, 6-phenyl-5-{4-[5-(4,4,4-trifluoro-butanesulfinyl)-pentyloxy]-phenyl}-8,9-dihydro-7H-benzocyclohepten-2-ol, 5-(4-{5-[methyl-(4,4,5,5,5-pentafluoropentyl)-amino]-pentyloxy}-phenyl)-6-phenyl-8,9-dihydro-7H-benzocyclohepten-2-ol, 5-[4-(5-benzylthio-pentyloxy)-phenyl]-6-phenyl-8,9-dihydro-7H-benzocyclohepten-2-ol, 5-[4-(5-benzylsulfinyl-pentyloxy)-phenyl]-6-phenyl-8,9-dihydro-7H-benzocyclohepten-2-ol, 5-{4-[5-(4-methyl-benzylthio)-pentyloxy]-phenyl}-6-phenyl-8,9-dihydro-7H-benzocyclohepten-2-ol, 5-{4-[5-(4-methyl-benzylsulfinyl)-pentyloxy]-phenyl}-6-phenyl-8,9-dihydro-7H-benzocyclohepten-2-ol, 6-phenyl-5-{4-[5-(4-trifluoromethyl-benzylthio)-pentyloxy]-phenyl}-8,9-dihydro-7H-benzocyclohepten-2-ol, 6-phenyl-5-{4-[5-(4-trifluoromethyl-benzylsulfinyl)-pentyloxy]-phenyl}-8,9-dihydro-7H-benzocyclohepten-2-ol, 6-phenyl-5-[4-(5-phenylthio-pentyloxy)-phenyl]-8,9-dihydro-7H-benzocyclohepten-2-ol, 6-phenyl-5-[4-(5-phenylsulfinyl-pentyloxy)-phenyl]-8,9-dihydro-7H-benzocyclohepten-2-ol, 6-phenyl-5-[4-(5-phenylsulfonyl-pentyloxy)-phenyl]-8,9-dihydro-7H-benzocyclohepten-2-ol, 5-{4-[5-(4-tert-butyl-phenylthio)-pentyloxy]-phenyl}-6-phenyl-8,9-dihydro-7H-benzocyclohepten-2-ol, 5-{4-[5-(4-tert-butyl-phenylsulfinyl)-pentyloxy]-phenyl}-6-phenyl-8,9-dihydro-7H-benzocyclohepten-2-ol, 5-{4-[5-(4-tert-butyl-phenylsulfonyl)-pentyloxy]-phenyl}-6-phenyl-8,9-dihydro-7H-benzocyclohepten-2-ol, 6-phenyl-5-{4-[5-(4-trifluoromethyl-phenylthio)-pentyloxy]-phenyl}-8,9-dihydro-7H-benzocyclohepten-2-ol, 6-phenyl-5-{4-[5-(4-trifluoromethyl-phenylsulfinyl)-pentyloxy]-phenyl}-8,9-dihydroxy-7H-benzocyclohepten-2-ol, 6-phenyl-5-{4-[5-(4-trifluoromethyl-phenylsulfonyl)-pentyloxy]-phenyl}-8,9-dihydro-7H-benzocyclohepten-2-ol, or a physiologically compatible salt thereof.

10. A pharmaceutical composition comprising at least one compound according to claim 1 and a pharmaceutically compatible vehicle.

11. A method for preparing a pharmaceutical composition comprising admixing a compound according to claim 1 and a pharmaceutically compatible vehicle.

12. A compound according to formula 1, wherein said compound is 5-{4-[5-(4,4,5,5,5-Pentafluoro-pentanesulfinyl)-pentyloxy]-phenyl}-6-phenyl-8,9-dihydro-7H-benzocyclohepten-2-ol or a physiologically compatible salt thereof.

13. A compound according to claim 1, wherein $R^1$ and $R^2$ are each independently H, OH, $C_1$–$C_{10}$ alkoxy, $C_1$–$C_{10}$ alkanoyloxy, or $C_7$–$C_{15}$ aroyloxy.

14. A compound according to claim 5, wherein $R^1$ and $R^2$ are each independently H, OH, $C_1$–$C_{10}$ alkoxy, $C_1$–$C_{10}$ alkanoyloxy, or $C_7$–$C_{15}$ aroyloxy.

15. A compound according to formula 6, wherein $R^1$ and $R^2$ are each independently H, OH, $C_1$–$C_{10}$ alkoxy, $C_1$–$C_{10}$ alkanoyloxy, or $C_7$–$C_{15}$ aroyloxy.

16. A compound according to formula 7, wherein wherein $R^1$ and $R^2$ are each independently H, OH, $C_1$–$C_{10}$ alkoxy, $C_1$–$C_{10}$ alkanoyloxy, or $C_7$–$C_{15}$ aroyloxy.

17. A compound according to claim 13, wherein $R^1$ and $R^2$ each independently H, OH, alkoxy, methoxy, ethoxy, propoxy, isopropoxy, butoxy, isobutoxy, tert-butoxy, pentoxy, isopentoxy, neopentoxy, heptyloxy, hexyloxy, decyloxy, formyl, acetyl, propionyl, isopropionyl or benzoyl.

18. A compound according to claim 1, wherein side chain Y is selected from the following group:

—O—$(CH_2)_5$S$(CH_2)_3$C$_2$F$_5$

—O—$(CH_2)_5$SO$(CH_2)$$(CH_2)_3$C$_2$F$_5$

—O—$(CH_2)_5$SO$_2$$(CH_2)_3$C$_2$F$_5$

—O—$(CH_2)_2$N$(CH_3)$—$(CH_2)_3$—S—$(CH_2)_3$C$_2$F$_5$

—O—$(CH_2)_2$N$(CH_3)$—$(CH_2)_3$—SO—$(CH_2)_3$C$_2$F$_5$

—O—$(CH_2)_5$S$(CH_2)$—C(O)N$(CH_3)$—$(CH_2)_3$CH$_3$

—O—$(CH_2)_5$SO$(CH_2)$—C(O)N$(CH_3)$—$(CH_2)_3$CH$_3$

—O—$(CH_2)_2$NH$(CH_2)$OH

—O—$(CH_2)_2$N$(CH_3)$—$(CH_2)_2$—SO$(CH_2)$—C(O)N$(CH_3)$—$(CH_2)_3$CH$_3$

—O—$(CH_2)_2$N$(CH_3)$—$(CH_2)_2$—SO$_2$$(CH_2)$—C(O)N$(CH_3)$—$(CH_2)_3$CH$_3$

—O—$(CH_2)_6$S$(CH_2)$—C(O)N$(CH_3)$—$(CH_2)_3$CH$_3$

—O—$(CH_2)_5$SO$(CH_2)$—C(O)N$(CH_3)$—$(CH_2)_3$CH$_3$

—O—CH$_3$

—O—$(CH_2)_5$—F

—O—$(CH_2)_4$—F

—O—$(CH_2)_3$—F

—O—$(CH_2)_2$—F

—O—$(CH_2)_5$—Cl

—O—$(CH_2)_4$—Cl

—O—$(CH_2)_3$—Cl

—O—$(CH_2)_2$—Cl

—O—$(CH_2)_6$S$(CH_2)_3$C$_2$F$_6$

—O—$(CH_2)_6$SO$(CH_2)_3$C$_2$F$_6$

—O—$(CH_2)_5$S$(CH_2)_2$C$_3$F$_7$

—O—$(CH_2)_4$S$(CH_2)_3$C$_2$F$_5$

—O—$(CH_2)_4$SO$(CH_2)_3$C$_2$F$_5$

—O—$(CH_2)_4$SO$_2$$(CH_2)_3$C$_2$F$_5$

—O—$(CH_2)_5$S$(CH_2)_4$—F

—O—$(CH_2)_5SO(CH_2)_4$—F
—O—$(CH_2)_5S(CH_2)_3$—$CF_3$
—O—$(CH_2)_5SO(CH_2)_3$—$CF_3$
—O—$(CH_2)_5$—$N(CH_3)$—$(CH_2)_3$—$C_2F_5$.

19. A compound according to claim 1, wherein side chain Y is selected from the following group:

—$(CH_2)_5N(CH_3)(CH_2)_3C_2F_5$
—$(CH_2)_5N(CH_3)(CH_2)_6C_2F_5$
—$(CH_2)_5N(CH_3)(CH_2)_7C_2F_5$
—$(CH_2)_5N(CH_3)(CH_2)_8C_2F_5$
—$(CH_2)_6N(CH_3)(CH_2)_6C_2F_5$
—$(CH_2)_6N(CH_3)(CH_2)_7C_2F_5$
—$(CH_2)_6N(CH_3)(CH_2)_8C_2F_5$
—$(CH_2)_5N(CH_3)(CH_2)_2C_4F_9$
—$(CH_2)_5N(CH_3)(CH_2)_3C_6F_{13}$
—$(CH_2)_5N(CH_3)(CH_2)_3C_8F_{17}$
—$(CH_2)_5N(CH_3)(CH_2)_6C_4F_9$
—$(CH_2)_5N(CH_3)(CH_2)_6C_6F_{13}$
—$(CH_2)_5N(CH_3)(CH_2)_6C_8F_{17}$
—$(CH_2)_5N(CH_3)H$
—$(CH_2)_5N(CH_3)(CH_2)_9H$
—$(CH_2)_9S(CH_2)_3C_2F_5$
—$(CH_2)_9SO(CH_2)_3C_2F_5$
—$(CH_2)_9SO_2(CH_2)_3C_2F_5$.

20. A method for performing male or female hormone replacement therapy in a patient comprising administering to said patient an effective amount of a compound according to claim 1.

21. A method according to claim 20, wherein said compound is administered in an amount of 0.01–10 mg/kg of body weight per day.

22. A method according to claim 20, wherein said compound is administered in an amount of 0.1–5 mg/kg of body weight per day.

23. A method according to claim 20, wherein said compound is administered in a daily dosage of 0.8–800 mg.

24. A method according to claim 20, wherein said compound is administered in a daily dosage of 8–400 mg.

25. A method according to claim 20, wherein said compound is administered in a dosage unit containing 0.4–400 mg of said compound.

26. A method according to claim 20, wherein said compound is 5-{4-[5-(4,4,5,5,5-Pentafluoro-pentanesulfinyl)-pentyloxy]-phenyl}-6-phenyl-8,9-dihydro-7H-benzocyclohepten-2-ol or a physiologically compatible salt thereof.

27. A method according to claim 21, wherein said compound is 5-{4-[5-(4,4,5,5,5-Pentafluoro-pentanesulfinyl)-pentyloxy]-phenyl}-6-phenyl-8,9-dihydro-7H-benzocyclohepten-2-ol or a physiologically compatible salt thereof.

28. A method according to claim 23, wherein said compound is 5-{4-[5-(4,4,5,5,5-Pentafluoro-pentanesulfinyl)-pentyloxy]-phenyl}-6-phenyl-8,9-dihydro-7H-benzocyclohepten-2-ol or a physiologically compatible salt thereof.

* * * * *

UNITED STATES PATENT AND TRADEMARK OFFICE
CERTIFICATE OF CORRECTION

PATENT NO.    : 6,495,607 B2
DATED         : December 17, 2002
INVENTOR(S)   : Rolf Bohlmann et al.

It is certified that error appears in the above-identified patent and that said Letters Patent is hereby corrected as shown below:

Column 43,
Line 58, reads "$R^7 R^8$," should read -- $R^7$ and $R^8$, --.

Column 44,
Line 23, reads "$R^7$ and $R^8$ in each case" should read -- $R^7$ and $R^8$ are in each case --.
Line 25, reads "-$NR^7R$," should read -- $NR^7R^8$, --

Column 47,
Line 17, reads "6phenyl" should read -- 6-phenyl --

Column 48,
Line 21, reads "wherein wherein" should read -- wherein --
Line 25, reads "$R^2$ each", should read -- $R^2$ are each --
Line 34, reads "-O-$(CH_2)_5SO(CH_2)(CH_2)_3C_2F_5$" should read -- -O-$(CH_2)_5SO(CH_2)_3C_2F_5$ --
Line 48, reads "-O-$(CH_2)_5SO(CH_2)$" should read -- -O-$(CH_2)_6SO(CH_2)$ --

Signed and Sealed this

Thirtieth Day of December, 2003

JAMES E. ROGAN
*Director of the United States Patent and Trademark Office*